(12) United States Patent
Sharpe et al.

(10) Patent No.: US 7,586,604 B2
(45) Date of Patent: Sep. 8, 2009

(54) OPTICAL APPARATUS

(75) Inventors: Jonathan C. Sharpe, Hamilton (NZ); Peter N. Schaare, Hamilton (NZ)

(73) Assignee: XY, Inc., Fort Collins, CO (US)

( * ) Notice: Subject to any disclaimer, the term of this patent is extended or adjusted under 35 U.S.C. 154(b) by 133 days.

(21) Appl. No.: 11/805,572

(22) Filed: May 22, 2007

(65) Prior Publication Data

US 2007/0285662 A1     Dec. 13, 2007

Related U.S. Application Data

(60) Division of application No. 10/990,648, filed on Nov. 16, 2004, now Pat. No. 7,221,453, which is a continuation of application No. 09/355,461, filed as application No. PCT/NZ98/00009 on Feb. 2, 1998, now Pat. No. 6,819,411.

(30) Foreign Application Priority Data

Jan. 31, 1997    (NZ)   .................... 314169

(51) Int. Cl.
    G01N 21/00    (2006.01)
    G01N 33/48    (2006.01)
(52) U.S. Cl. ................... 356/338; 356/39
(58) Field of Classification Search ........... None
    See application file for complete search history.

(56) References Cited

U.S. PATENT DOCUMENTS

| | | |
|---|---|---|
| 3,005,756 A | 10/1961 | VanDemark et al. |
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |

(Continued)

FOREIGN PATENT DOCUMENTS

| | | |
|---|---|---|
| BR | 9704313 | 4/1999 |
| BR | 9704313 | 6/1999 |
| CA | 1029833 | 4/1978 |
| CA | 1 250 808 | 3/1989 |
| CA | 2113957 A1 | 1/1994 |

(Continued)

OTHER PUBLICATIONS

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

(Continued)

*Primary Examiner*—Gregory J Toatley, Jr.
*Assistant Examiner*—Amanda H Merlino
(74) *Attorney, Agent, or Firm*—Santangelo Law Offices P.C.

(57) ABSTRACT

Various optical apparatus, in particular embodiments, may provide a source of parallel light (7, 75). The parallel light (7, 75) may be generally achieved by directing an incident beam at the apex of a prism (1, 22, 24, 26, 28). The prism may have varying configurations. One configuration has a forward conical face (24). Another configuration has a pyramidal forward end (22). Other configurations are also disclosed. Various optical methods and methods for flow cytometry are also disclosed.

36 Claims, 11 Drawing Sheets

U.S. PATENT DOCUMENTS

| | | |
|---|---|---|
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,916,143 A | 10/1975 | Farrell |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,251,733 A * | 2/1981 | Hirleman, Jr. ............... 250/575 |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |

| | | |
|---|---|---|
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth et al. |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |
| 5,317,162 A | 5/1994 | Pinsky et al. |
| 5,336,217 A | 8/1994 | Buys et al. |
| 5,346,990 A | 9/1994 | Spaulding |
| RE34,782 E | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A | 5/1995 | Ogino |
| 5,437,987 A | 8/1995 | Ten et al. |
| 5,439,362 A | 8/1995 | Spaulding |
| 5,444,527 A | 8/1995 | Kosaka |
| 5,447,841 A | 9/1995 | Grey et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | Van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Atheyde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,578,449 A | 11/1996 | Fr asch et al. |
| 5,579,159 A | 11/1996 | Ito |
| 5,584,982 A | 12/1996 | Dovichi et al. |
| 5,589,457 A | 12/1996 | Wiltbank |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Gourley et al. |
| 5,620,842 A | 4/1997 | Davis et al. |
| 5,622,820 A | 4/1997 | Rossi |
| 5,627,037 A | 5/1997 | Ward et al. |
| 5,633,503 A | 5/1997 | Kosaka |
| 5,641,457 A | 6/1997 | Vardanega |
| 5,643,796 A | 7/1997 | Van den Engh et al. |
| 5,650,847 A | 7/1997 | Maltsev et al. |
| 5,658,751 A | 8/1997 | Yue et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,699,152 A * | 12/1997 | Fedor et al. ............... 356/240.1 |
| 5,700,692 A | 12/1997 | Sweet |
| 5,701,012 A | 12/1997 | Ho |
| 5,707,808 A | 1/1998 | Roslaniec et al. |
| 5,708,868 A | 1/1998 | Ishikawa |
| 5,712,807 A | 1/1998 | Bangham |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |
| 5,726,751 A | 3/1998 | Altendorf et al. |

| Patent | Date | Inventor |
|---|---|---|
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | den Engh et al. |
| 5,759,767 A | 6/1998 | Lakowicz et al. |
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,796,112 A | 8/1998 | Ichie |
| 5,798,276 A | 8/1998 | Haugland et al. |
| 5,799,830 A | 9/1998 | Carroll et al. |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,831,723 A | 11/1998 | Kubota et al. |
| 5,835,262 A | 11/1998 | Iketaki et al. |
| 5,840,504 A | 11/1998 | Blecher |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A | 2/1999 | Paisson |
| 5,876,942 A | 3/1999 | Cheng et al. |
| 5,880,457 A | 3/1999 | Tomiyama et al. |
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Prather et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,973,842 A | 10/1999 | Spangenberg |
| 5,985,216 A | 11/1999 | Rens et al. |
| 5,985,538 A | 11/1999 | Stachecju |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | Van den Engh |
| 6,042,025 A | 3/2000 | Crampton et al. |
| 6,042,249 A | 3/2000 | Spangenberg |
| 6,050,935 A | 4/2000 | Ranoux et al. |
| 6,071,689 A | 6/2000 | Seidel et al. |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan et al. |
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Paisson |
| 6,143,901 A | 11/2000 | Dervan |
| 6,146,837 A | 11/2000 | van de Winkel |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,207,392 B1 | 3/2001 | Weiss et al. |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 | 7/2001 | Buchanan et al. |
| 6,283,920 B1 | 9/2001 | Eberle et al. |
| 6,296,810 B1 | 10/2001 | Ulmer |
| 6,309,815 B1 | 10/2001 | Tash et al. |
| 6,316,234 B1 | 11/2001 | Bova |
| 6,317,511 B1 | 11/2001 | Horiuchi |
| 6,322,901 B1 | 11/2001 | Bawendi et al. |
| 6,323,632 B1 | 11/2001 | Husher et al. |
| 6,326,144 B1 | 12/2001 | Bawendi et al. |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon et al. |
| 6,372,422 B1 | 4/2002 | Seidel et al. |
| 6,372,506 B1 | 4/2002 | Norton |
| 6,384,951 B1 | 5/2002 | Basiji et al. |
| 6,395,305 B1 | 5/2002 | Buhr et al. |
| 6,400,453 B1 | 6/2002 | Hansen |
| 6,411,835 B1 | 6/2002 | Modell et al. |
| 6,411,904 B1 | 6/2002 | Chandler |
| 6,416,190 B1 | 7/2002 | Grier et al. |
| 6,423,505 B1 | 7/2002 | Davis |
| 6,423,551 B1 | 7/2002 | Weiss et al. |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Paisson et al. |
| 6,524,860 B1 | 2/2003 | Seidel et al. |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,563,583 B2 | 5/2003 | Ortyn et al. |
| 6,576,291 B2 | 6/2003 | Bawendi et al. |
| 6,577,387 B2 | 6/2003 | Ross, III et al. |
| 6,580,504 B1 | 6/2003 | Ortyn et al. |
| 6,587,203 B2 | 7/2003 | Colon |

| | | |
|---|---|---|
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 | 11/2003 | Koller et al. |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B2 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 5/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,286 B2 | 7/2004 | Py et al. |
| 6,761,288 B2 | 7/2004 | Garcia |
| 6,767,706 B2 | 7/2004 | Quake |
| 6,780,377 B2 | 8/2004 | Hall et al. |
| 6,782,768 B2 | 8/2004 | Buchanan et al. |
| 6,789,706 B2 | 9/2004 | Abergel et al. |
| 6,789,750 B1 | 9/2004 | Heldt |
| 6,793,387 B1 | 9/2004 | Neas et al. |
| 6,813,017 B1 | 11/2004 | Hoffman et al. |
| 6,819,411 B1 | 11/2004 | Sharpe et al. |
| 6,849,394 B2 | 2/2005 | Rozeboom et al. |
| 6,849,423 B2 | 2/2005 | Mutz et al. |
| 6,861,265 B1 | 3/2005 | Van den Engh |
| 6,941,005 B2 | 9/2005 | Lary et al. |
| 7,015,310 B2 | 3/2006 | Remington et al. |
| 7,094,527 B2 | 8/2006 | Seidel et al. |
| 7,105,355 B2 | 9/2006 | Kurabayashi et al. |
| 7,195,920 B2 | 3/2007 | Seidel et al. |
| 7,208,265 B1 | 4/2007 | Schenk |
| 7,221,453 B2 | 5/2007 | Sharpe |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier et al. |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Ozasa et al. |
| 2002/0171827 A1 | 11/2002 | Van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0098421 A1 | 5/2003 | Ho |
| 2003/0113765 A1 | 6/2003 | Dempcy et al. |
| 2003/0119050 A1 | 6/2003 | Shai |
| 2003/0119206 A1 | 6/2003 | Shai |
| 2003/0129091 A1 | 7/2003 | Seidel et al. |
| 2003/0157475 A1 | 8/2003 | Schenk |
| 2003/0165812 A1 | 9/2003 | Takayama et al. |
| 2003/0175917 A1 | 9/2003 | Cumming |
| 2003/0175980 A1 | 9/2003 | Hayenga et al. |
| 2003/0190681 A1 | 10/2003 | Shai |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0034879 A1 | 2/2004 | Rothstein et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0061070 A1 | 4/2004 | Hansen |
| 2004/0061853 A1 | 4/2004 | Blasenheim |
| 2004/0062685 A1 | 4/2004 | Norton et al. |
| 2004/0072278 A1 | 4/2004 | Chou et al. |
| 2004/0107150 A1 | 6/2004 | Neas et al. |
| 2004/0132001 A1 | 7/2004 | Seidel et al. |
| 2005/0003472 A1 | 1/2005 | Anzar et al. |
| 2005/0011582 A1 | 1/2005 | Haug |
| 2005/0064383 A1 | 3/2005 | Bashkin et al. |
| 2005/0112541 A1 | 5/2005 | Durack et al. |
| 2005/0214733 A1 | 9/2005 | Graham |
| 2005/0244805 A1 | 11/2005 | Ludwig et al. |
| 2005/0282245 A1 | 12/2005 | Ludwig et al. |
| 2006/0118167 A1 | 6/2006 | Neas et al. |
| 2006/0203226 A1 | 9/2006 | Roche et al. |
| 2006/0263829 A1 | 11/2006 | Evans et al. |
| 2006/0281176 A1 | 12/2006 | Seidel et al. |
| 2007/0026378 A1 | 2/2007 | Schenk |
| 2007/0026379 A1 | 2/2007 | Seidel et al. |
| 2007/0042342 A1 | 2/2007 | Seidel et al. |
| 2007/0092860 A1 | 4/2007 | Schenk |
| 2007/0099260 A1 | 5/2007 | Seidel et al. |
| 2007/0117086 A1 | 5/2007 | Evans et al. |
| 2007/0123461 A1 | 5/2007 | Josephson |
| 2007/0248976 A1 | 10/2007 | Harding |

FOREIGN PATENT DOCUMENTS

| | | |
|---|---|---|
| CN | ZL 03109426.0 | 12/2005 |
| DE | 69028526 | 2/1997 |
| DE | 195 49 015 C1 | 4/1997 |
| DE | 198 82 943.3 | 2/2001 |
| EP | 0025296 A2 | 3/1981 |
| EP | 0 046 345 A2 | 2/1982 |
| EP | 0 068 404 B1 | 1/1983 |
| EP | 0071538 A1 | 2/1983 |
| EP | 0 026 770 B1 | 3/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0160201 A2 | 11/1985 |
| EP | 0189702 A1 | 8/1986 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0461618 | 12/1991 |
| EP | 0 463 562 A1 | 1/1992 |
| EP | 0468100 A1 | 1/1992 |
| EP | 0474 187 A2 | 3/1992 |
| EP | 0 316 172 B1 | 7/1992 |
| EP | 0 316 171 B1 | 9/1992 |
| EP | 0570102 A | 3/1993 |
| EP | 0538786 A | 4/1993 |
| EP | 0 279 000 B1 | 7/1993 |

| | | | | | | |
|---|---|---|---|---|---|---|
| EP | 0 553 951 A1 | 8/1993 | | WO | WO 91/05236 | 4/1991 |
| EP | 0 288 029 B1 | 1/1994 | | WO | WO 92/08120 A1 | 5/1992 |
| EP | 0 381 694 B1 | 6/1994 | | WO | WO 92/17288 A1 | 10/1992 |
| EP | 0 361 504 B1 | 7/1994 | | WO | WO 93/10803 | 6/1993 |
| EP | 606847 A2 | 7/1994 | | WO | WO 9317322 A1 | 9/1993 |
| EP | 0 289 200 B2 | 8/1994 | | WO | WO 94/22001 A1 | 9/1994 |
| EP | 0 555 212 B1 | 10/1994 | | WO | WO 96/04542 A1 | 2/1996 |
| EP | 0 361 503 B1 | 11/1994 | | WO | WO 96/12171 A2 | 4/1996 |
| EP | 0 696 731 A2 | 2/1996 | | WO | WO 96/12172 | 4/1996 |
| EP | 0 705 978 A2 | 4/1996 | | WO | WO 96/12173 A1 | 4/1996 |
| EP | 0 711 991 A1 | 5/1996 | | WO | WO 96/31764 | 10/1996 |
| EP | 0 471 758 B1 | 9/1996 | | WO | WO 96/33806 A1 | 10/1996 |
| EP | 0 736 765 A1 | 10/1996 | | WO | WO 97/29354 A1 | 8/1997 |
| EP | 0 545 284 B1 | 2/1997 | | WO | WO 97/30338 A1 | 8/1997 |
| EP | 0 360 487 B1 | 7/1997 | | WO | WO 97/35189 A1 | 9/1997 |
| EP | 0 412 431 B1 | 10/1997 | | WO | WO 98/34094 A1 | 8/1998 |
| EP | 0 526 131 B1 | 1/1998 | | WO | WO 98/48259 | 10/1998 |
| EP | A-0 478155 | 1/1998 | | WO | WO 98/57152 A1 | 12/1998 |
| EP | 0 822 404 A3 | 2/1998 | | WO | WO 99/05504 A2 | 2/1999 |
| EP | 0 822 401 A2 | 4/1998 | | WO | WO 99/33956 A1 | 7/1999 |
| EP | 0781985 A3 | 7/1998 | | WO | WO 99/38883 A1 | 8/1999 |
| EP | 0 556 748 B1 | 10/1998 | | WO | WO 99/42810 A1 | 8/1999 |
| EP | 0 430 402 B1 | 1/1999 | | WO | WO 99/44035 | 9/1999 |
| EP | 0 529 666 B1 | 4/2000 | | WO | WO 99/44037 A1 | 9/1999 |
| EP | 0 994 342 A3 | 4/2000 | | WO | WO 99/47906 A1 | 9/1999 |
| EP | 0 752 133 B1 | 6/2000 | | WO | WO 99/60397 A1 | 11/1999 |
| EP | 1 018 644 A2 | 7/2000 | | WO | WO 9957955 | 11/1999 |
| EP | 1 118 268 A1 | 7/2001 | | WO | WO 99/61888 A2 | 12/1999 |
| EP | 1 147 774 A1 | 10/2001 | | WO | WO 00/06193 A1 | 2/2000 |
| EP | 0 534 033 B1 | 11/2001 | | WO | WO 00/12204 | 3/2000 |
| EP | 0 925 494 B1 | 12/2001 | | WO | WO 00/36396 | 6/2000 |
| EP | 0 748 316 B1 | 5/2002 | | WO | WO 00/49387 | 8/2000 |
| EP | 0 662 124 B1 | 6/2002 | | WO | WO 00/54026 | 9/2000 |
| EP | 1 245 944 A3 | 10/2002 | | WO | WO 00/56444 | 9/2000 |
| EP | 1 249 502 A2 | 10/2002 | | WO | WO 00/70080 | 11/2000 |
| EP | 1250897 A1 | 10/2002 | | WO | WO 01/02836 A1 | 1/2001 |
| EP | 1 380 304 A2 | 1/2004 | | WO | WO 01/28700 A1 | 4/2001 |
| EP | 1403633 A3 | 4/2004 | | WO | WO 01029538 | 4/2001 |
| EP | 1 100 400 B1 | 5/2004 | | WO | WO 01/37655 A1 | 5/2001 |
| EP | 1 257 168 B1 | 2/2005 | | WO | WO 01/40765 A2 | 6/2001 |
| FR | 2574656 A1 | 6/1986 | | WO | WO 01/40765 A3 | 6/2001 |
| FR | A-2 635453 | 2/1990 | | WO | WO 01/42757 A2 | 6/2001 |
| FR | 2 647 668 A | 12/1990 | | WO | WO 01/51612 A1 | 7/2001 |
| FR | 2699678 A1 | 6/1994 | | WO | WO 01/61313 A2 | 8/2001 |
| GB | 2 121 976 A | 1/1984 | | WO | WO 01/68110 | 9/2001 |
| GB | 2 122 369 A | 1/1984 | | WO | WO 01/68226 A2 | 9/2001 |
| GB | 2 125 181 A | 2/1984 | | WO | WO 01/71348 A1 | 9/2001 |
| GB | 2 136 561 A | 9/1984 | | WO | WO 01/75161 A2 | 10/2001 |
| GB | 2 137 352 A | 10/1984 | | WO | WO 0175176 | 10/2001 |
| GB | 2145112 | 2/1985 | | WO | WO 01/85913 A2 | 11/2001 |
| GB | 2 144 542 A | 3/1985 | | WO | WO 01/85913 A3 | 11/2001 |
| GB | 2 153 521 A | 8/1985 | | WO | WO 01/90295 A1 | 11/2001 |
| GB | 2 243 681 A | 11/1991 | | WO | WO 01/95815 A1 | 12/2001 |
| GB | 1471019 | 4/1997 | | WO | WO 02/01189 A1 | 1/2002 |
| GB | 2 360 360 A | 9/2001 | | WO | WO 02/04666 A2 | 1/2002 |
| JP | 61139747 (A) | 6/1986 | | WO | WO 02/19594 | 3/2002 |
| JP | 61159135 (A) | 7/1986 | | WO | WO 02/19943 A1 | 3/2002 |
| JP | 2024535 | 1/1990 | | WO | WO 02/20850 A2 | 3/2002 |
| JP | 4126064 (A) | 4/1992 | | WO | WO 02/21102 A2 | 3/2002 |
| JP | 4126065 (A) | 4/1992 | | WO | WO 02/23163 A1 | 3/2002 |
| JP | 4126066 (A) | 4/1992 | | WO | WO 02/25269 A2 | 3/2002 |
| JP | 4126079 (A) | 4/1992 | | WO | WO 02/26114 A2 | 4/2002 |
| JP | 4126080 (A) | 4/1992 | | WO | WO 02/28311 A1 | 4/2002 |
| JP | 4126081 (A) | 4/1992 | | WO | WO 02/29106 A2 | 4/2002 |
| SU | 1056008 | 11/1983 | | WO | WO 02/41906 A2 | 5/2002 |
| SU | 1260778 A1 | 9/1986 | | WO | WO 02041906 A2 | 5/2002 |
| WO | WO 84/01265 A1 | 4/1984 | | WO | WO 02/43486 A1 | 6/2002 |
| WO | WO 85/04014 A1 | 9/1985 | | WO | WO 02/43574 A3 | 6/2002 |
| WO | WO 88/07198 | 9/1988 | | WO | WO 02/44319 A2 | 6/2002 |
| WO | WO 89/04470 A1 | 5/1989 | | WO | WO 02/052244 A2 | 7/2002 |
| WO | WO 89/04471 A1 | 5/1989 | | WO | WO 02/054044 A2 | 7/2002 |
| WO | WO 89/04472 A1 | 5/1989 | | WO | WO 02/057775 A1 | 7/2002 |
| WO | WO 90/13315 A1 | 11/1990 | | WO | WO 02/060880 A1 | 8/2002 |

| | | |
|---|---|---|
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | WO 03020877 A2 | 3/2003 |
| WO | WO 03/056330 A2 | 7/2003 |
| WO | WO 03/056335 A2 | 7/2003 |
| WO | WO 03/072765 A1 | 9/2003 |
| WO | WO 03/078065 A1 | 9/2003 |
| WO | WO 03/078972 A1 | 9/2003 |
| WO | WO 04001401 | 12/2003 |
| WO | WO 2004/006916 A1 | 1/2004 |
| WO | WO 2004/009237 A2 | 1/2004 |
| WO | WO 2004/009237 A3 | 1/2004 |
| WO | WO 2004/012837 A2 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/024227 A3 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006/015056 A2 | 2/2006 |
| WO | WO 2006012597 A2 | 2/2006 |
| WO | WO 2006060770 A2 | 8/2006 |
| WO | WO 2007/016090 A2 | 2/2007 |

OTHER PUBLICATIONS

Akhtar, S., et al., "Prevalence of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P. et al., "Issues Affecting Commercialization of Sexed Sperm" Therio. 52:1441. (1999).
Amann, R. P., et al., "Prospects For Sexing Mammalian Sperm," Animal Reproduction Laboratory College of Veterinary Medicine and Biomedical Sciences, Colorado State University. (1982).
Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).
Anderson, V. K., et al., Intrauterine und tiefzervikale Insemination mit Gefriersperma bein Schat (Intrauterine and Deep Cervical Insemination With Frozen Semin in Sheep). Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cytometer," University of Washington Feb. 19, 1996.
Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1): 359 (1998).
Beyhan, Z., et al., 1999 Sexual Dimorphism In IVM-IVF Bovine Embryos Produced from X and Y Chromosome-Bearing Spermatozoa Sorted By High Speed Flow Cytometry. Theriogenology. 52: 35-48.
Bigos, Martin "Nine Color Eleven Parameter Immunophenotyping Using Three Laser Flow Cytometry," Stanford University Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sci. 65:963. 1987.
Bracher, V. and Allen, W.R., "Videoendoscopic Examination of the Mare's Uterus: I. Findings in Normal Fertile Mares", Equine Veterinary Journal, vol. 24, p. 274-278. 1992.
Braselton, W. E. and McShan, W. H., "Purification and Properties of Follicle Stimulating and Luteinizing Hormones From Horse Pituitary Glands" Arch. Biochem. Biophys. 139:45-48, 1970.
Braun, J. et al, "Effect of Different Protein Supplements on Motility and Plasma Membrane Integrity of Frozen- Thawed Stallion Spermatozoa", Cryobiology (1995) 32:487-492.
Brethour, J. R. and Jaeger, J. R., "The Single Calf Heifer System", Kansas Agric. Sta. Rep of Progress 570. 1989.
Brinsko, S.P. et al., "Artificial Insemination and Preservation of Semen." Veterinary Clinics of North America:Equine Practice vol. 8 Num.1 Apr. 1992 pp. 205-218.
Bristol, F. "Breeding Behavior of a Stallion at Pasture With 20 Mares in Synchronized Oestrus" J. Reprod. Fertil. Suppl. 32:71. 1982.
Brookes, A. J. and O'Byrne, M., "Use of Cow-Heifers in Beef Production" J. of the Royal Agricultural Society of England 126:30. 1965.

Buchanan, B. R., et al., "Insemination of Mares with Low Numbers of Either Unsexed or Sexed Spermatozoa", Therio. vol. 53, p. 1333-1344. 2000.

Buchanan, B.R. "Pregnancy Rates in Mares Following a Single Insemination with a Low Number of Spermatozoa into the Tip of the Uterine Horn" Theriogenology p. 395 1999.

Burns, P. D. and Spitzer, J.C., "Influence of Biostimulation on Reproduction in Postpartum Beef-Cows", J. Anim. Sci. 70:358. 1992.

Burwash, L D., et al., "Relationship of Duration of Estrus to Pregnancy Rate in Normally Cyclings, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

Celestron: Telescope Basics: www.celestron.com/tb-2ref/htm; 4 pages, Oct. 20, 2003.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52. p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al, "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonography* 1st ed. Rantanen, N.W. and McKinnon A.O. (eds.) Williams and Williams, 1998, p. 165-69.

da Silva, Coutinho M.A.. "Effect of time of oocyte collection and site of insemination on oocyte transfer in mares." Animal Reproduction and Biotechnology Laboratiory, Colorado State University, Fort Collins Journal of Animal Science 2002. 80:1275-1279.

*DakoCytomation*, "*MoFlo® Sorters*" http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Diagnositc Products Corporation, "*Coat-A-Count*" http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (*Panthera tigris*)" J. Reprod. Fertil. 107:53-58, 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D. W. et at. Analysis of DNA content of Living Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272.1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1996 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are The Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408. 1962.

Fugger, E. F. "Clinical Experience with Flow Cytometric Separation of Human X- and Y-Chromosome Bearing Sperm", Therio. vol. 52, pp. 1435-1440.1999.

Fuller, Robert R. "Characterizing Submicron Vesicles With Wavelength-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orienatation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." j. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper -Mayer"; Zbechr. F. Phys. 47 S. 509 1928.

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. Abstract Complete article from Reproductive Technology vol. 12 # Apr. 1, 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspect of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu, "*Technical Information, Optical Detector Selection: A Delicate Balancing Act*", web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," Sci. Am. 1976; 234, pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine." Science, Oct. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious furo*) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ratio in Semen Purportedly Enriched for X or Y Bearing Spermatozoa", Therio. 1988 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al. "Sex Preselection: High-speed Flow Cytometric Sorting of X and Y Sperm for Maximum Efficiency", Therio. vol. 52, p. 1323-1341 (1999).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytometry of X- and Y-Chromosome Bearing Sperm for DNA Using an Improved Preparation Method and Staining with Hoechst 33342." Garnete Research 17: 203-212. (1987).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemsitry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modelling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle-Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogeneology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semin." J S Afr. Vet. Assoc. 56(2): 61-63. (1985).

Levinson, G., et al., "DNA-based X-Enriched Sperm Separations as an Adjunct to Preimplantation Genetic Testing for the Preparation of X-linked Disease." Mol. Human Reprod. 10:979-982. (1995).

Lightwave Electronics, "Xcyte," www.LightwaveElectronics.com.

Lindsey, A. C., et al., "Low Dose Insemination of Mares Using Non-Sorted and Sex-Sorted Sperm" Animal Reproduction Science 68 p. 279-89 (2001).

Lindsey, A., et al., "Hysteroscopic Insemination of Mares with Nonfrozen Low-dose Unsexed or Sex-sorted Spermatozoa", pp. 1-15, 2000.

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. 2001 abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy," 1996 Biophotonics International.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Candian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)," Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) The Early Calving of Heifers and its Impact on Beef Production. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1183 (1990).

McKinnon, A.O. and Voss, J. L. Equine Reproduction. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Moleucular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 1971 54:548.

Molinia, F. C., et al., "Successful Fertilization After Superovulation and Laparoscopic Intrauterine Insemination of the Brushtail Possum Trichosurus vulpecula, and Tammar Wallaby, Macropus eugenii." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Suppl. 1) 64:158.

Olive, M.D., "Detection of Enterotoxigenic Escherichia coli after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 2001, 23:115-121.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., Recent Developments in Artificial Inseminatin in Horses Livestock Production Science, 1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143 (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115-118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Reiger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Vitro Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads + Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) ( 1961 & 1978 Combined) Chapters 16 and 17 are the complete article.

Schenk, J. L. "Applying Semen Sexing Technology to the AI Industry", Proceedings of the 18th Technical Conference on Artificial insemination & Reproduction, 2000.

Schenk, J. L, et al., "Imminent Commercialization of Sexed Bovine Sperm", Proceedings, The Range Beef Cow Symposium XVL, p. 89-96 (1999).

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination", 7th International Symposium On Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195 (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., et al, "Insemination Of Heifers With Very Low Numbers Of Frozen Spermatozoa", CSU, Atlantic Breeders Cooperative, Lancaster, PA, DUO Dairy, Loveland, CO, Jul. 1996.

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio. vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Imporant Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997, Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14. 2002.

Spectra-Physics, The Solid State Laser Company, Vanguard 2000-HMD 532, www.spectra-physics.com, Copyright 2002.

Spectra-Physics, The Solid State Laser Company, Vanguard 350-HMD 355, www.spectra-physics.com Copyright 2002.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", (1998) pp. 1, 39-41, 81-89.

Staigmiller, R.B. "Superovulation of Cattle with Equine Pituitary Extract and Porcine FSH" Theriogenology 37: 1091-1099 1992.

Stap J. et al Improving the Resolution of Cryopreserved X- and Y-Sperm During DNA Flow Cytometric Analysis with the Addition of Percoll to quench the Fluorescence of Dead Sperm: Academic Medical Center, Univeristy of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

Time-Bandwidth Products "GE—100—XHP", www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., "Geslachtsbepaling met interferometrie", Derde prijs NtvN-prijsvraag voor pas-gepromoveerden 65/4, (Sex Determination with Interferometry) p. 95-98 (1999).

van Munster, E. B., et al, "Difference in Sperm Head Volume as a Theoretical Basis for Sorting X & Y-Bearing Spermatozoa: Potentials and Limitations", Therio 52, pp. 1281-1293 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine: New Strategy for Deep Insemination with Low Number of Spermatozoa Using a Non-surgical Methodology", 14th International Congress on Animal Reproduction, vol. 2, Stockholm, Jul. 2000, p. 289.
Vazquez, J., et al., "Development of a Non-surgical Deep Intra Uterine Insemination Technique", Boar Semen Preservation IV, IVth International Conference on Boar Semen Preservation, Maryland, Aug. 8, 1999, pp. 262-263.
Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263., Jun. 2004.
Vazquez, J., et al., "Successful low dose insemination by a fiber optic Endoscope technique in the Sow", Proceedings Annual Conferene of the International Embryo Transfer Society, Netherlands, Theriogenology, vol. 53 Jan. 2000.
Vidament, M., et al., "Equine Frozen Semen Freezability and Fertility Field Results." Therio. 48:907. (1997).
Vincent, B.C., et al, "Carcass Characteristics and Meat Quality of Once-Calved Heifers." Canadian J. Anim. Sci. 71:311. (1991).
Vogel, T., et al, "Organization and Expression of Bovine TSPY", Mammalian Genoma, vol. 8, pp. 491-496 (1997).
Voss, J. L. and Pickett, B. W., "Reproductive Management of the Broodmare." CSU Exp. Sta. Anim. Reprod. Lab. Gen. Series. Bull. 961. (1976).
Voss, J. L., et al., "Effect of Number and Frequency of Inseminations on Fertility in Mares." J. Reprod. Fertil. Suppl. 32:53-57. (1982).
Voss, J. L., et al., Effect of Human Chorionic Gonadotropin on Duration of Estrous Cycle and Fertility of Normally Cycling, Nonlactating Mares. J.A.V.M.A. 165:704-706. (1974).
Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.
Watson, "Recent Developments and Concepts in the Cryopreservvation of Spermatozoa and the Assessment of Their Post-Thawing Function," Reprod. Fertil. Dev. 7:871-891 (1995) Abstract.
Welch G., et al., Fluidic and Optical Modifications to a FACS IV for Flow Sorting of X- and Y-Chromosome Bearing Sperm Based on DNA. Cytometry 17 (Suppl. 7): 74. (1994).
Welch, G., et al., "Flow Cytometric Sperm Sorting and PCR to Confirm Separation of X- and Y-Chromosome Bearing Bovine Sperm", Animal Biotechnology, 6, pp. 131-139 (1995).
Wheeler, T. L., et al., "Effect of Marbling Degree on Beef Palatability in Bos-taurus and Bos-indicus cattle." J. Anim. Sci. 72:3145. (1994).
Wickersham, E. W. and L. H. Schultz. "Influence of Age at First Breeding on Growth, Reproduction, and Production of Well-Fed Holstein Heifers." J. Dairy Sci. 46:544. (1963).
Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.
Wilson, C. G., et al., "Effects of Repeated hCG Injections on Reproductive Efficiency in Mares." Eq. Vet. Sci. 4:301-308. (1990).
Wilson, D. E. et al., "Mammal Species of the World", Smithsonian Institution Press, 1993, 1206 pp.
Wilson, M.S. "Non-surgical Intrauterine Artificial Insemination in Bitches Using Frozen Semen." J. Reprod. Fertil. Suppl. 47:307-311. (1993).
Windsor, D. P., et al, "Sex Predetermination by Separation of X and Y Chromosome-bearing Sperm: A Review", Reproduction of Fertilization and Development 5, pp. 155-171, (1993).
Wintzer et al.:"Krankheiten des Pferdes Ein Leitfaden fur Studium und Praxiz," 1982, nParey, Berlin Hamburg XP002281450.
Woods, G. L. and Ginther, O. J. "Recent Studies Related to the Collection of Multiple Embryos in Mares." Therio. 19:101-108. (1983).
Woods, J., et al., "Effects of Time of Insemination Relative to Ovulation on Pregnancy Rate and Embryonic-Loss Rate in Mares." Eq. Vet. J. 22(6): 410-415. (1990).
Zhou, Hongwei, et al. "Research on and Development of Flow Cell Sorting Apparatuses," Gazette of Biophysics, vol. 13, ed. 3, 1997.
Hamamatsu, *Photomultiplier Tubes*," web page, http://www.optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1995).
Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.
Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.
Hollinshead F. K. et al. "Production of lambs of predetermined sex after the insemination of ewes with low numbers of frozen-thawed sorted X- and Y- Chromosome-bearing spermatozoa", Reprod. Fertil. And Develop. 2002, vol. 14, pp. 503-508.
Hollinshead F. K. et al. "Sex-Sorting and Re-cryopreservation of Frozen-Thawed Ram Sperm for In Vitro Embryo Production" Theriogenology, vol. 59. (2003) pp. 209.
Dhali et al. Verification of Buffalo (Bubalus Bubalis)Oocytes, Embryo Theriogenology vol. 53, pp. 1295-1303 (2000).
Borini et al. Cryopreservation of Mature Oocytes: The us of a trypsin inhibitor enhances fertilization and obtained embryos rates, Fertil. Steril. (1997), vol. 68 (Suppl.).
Hamamatsu Photonics K.K. Electronic Tube Center, Photomultiplier Tubes, Brochure Dec. 1997.
Johnson, L. A., et al. The Beltsville Sperm Sexing Technology: High-speed sperm sorting gives improved sperm output for In Vitro fertilization and AI, Journal of Animal Science,vol. 77, Suppl 2/J, Dairy Sci. vol. 82, Suppl. Feb. 1999 pp. 213-220.
Peters D., The LLNL high-speed sorter: Design features,operational characteristics, and bioloical utility, Cyometry, 6:290-301 (1985).
Rens W., et al Slit-scan flow cytometry for consistent high resdolution DNA analysis of X- and Y- chromosome bearing sperm, Cytometry 25:191-199 (1996).
van Munster, E. B. Interferometry in flor to sort unstained X- and Y-Chromosome-Bearing Bull Spermatozoa, Cytometry 47:192-199 (2002).
Scmid, R. L. et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.
Brink, Z et al. A reliable procedure for superovulating cattle to obtain zygotes and early emryos for microinjection, Theriogenology vol. 41, p. 168, (1994).
Spectra-Physics, The Solid State Laser Company, Vanguard 350-HMD 355, User's Manual, Dec. 2002.
Photon, Inc. Light MeasuringSolutions, NanoScan for High-powered beam Applications, 2005.
Fluorescense Lifetime Systems, www.picoquant.com, Jan. 28, 2005 pp. 2.
NCI ETI Branch, Flow CytometryCore Laboratory, http://home.ncifcrf.gov/ccr/flowcore/ndyag.htm, pp. 5, May 11, 2004.
NCI ETI Branch, Flow CytometryCore Laboratory, http://home.ncifcrf.gov/ccr/flowcore/lsrll.htm, pp. 14, May 11, 2004.
Saacke,R.G., Can Spermatozoa with abnormal heads gain access to the ovum in artificially inseminated super- and single-ovulating cattle?, Theriogenology 50:117-128. 1998.
Hawk, H.W., Gamete Transport in the Superovulated Cow. Theriogenology: Jan. 1998 vol. 29 No. 1 pp. 125-142.
Blecher, S.R., et al. A new approach to immunological sexing of sperm, Theriogenology, 59, pp. 1309-1321, 1999 Vol.
Wheeler, M. B., et al. Application of sexed semen technology to in vitro embryo production in cattle, Theriogenology, vol. 65 (2006) 219-227.
Garverick, H. A., et al. mRNA and protein expression of P450 aromatase (AROM) and estrigen receptors (ER) $\alpha$ and $\beta$ during early development of bovine fetal ovaries; The society for the study of reproduction 38th annual meeting Jul. 24-27, 2005; Abstract only.
Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann, F. A., et al., Validation of sperm sexing in the cattle (Bos taurus) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Scinece; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technology's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Diary Industry $IN Asia B. Japan; www.agnet.org/library/article/eb384b.html.

Crichton,E. et al., 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept of Agri.

De Vries, A. Economic Value of Pregnancy in Diary Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reproduction, vol. 53, pp. 276-284.

Salisbury, G.W. et al., Substrate-Free Epididymal-Like Bovine Spermatozoa, J Reprod Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Aquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration of β-D-Glucuron idase Activity as Indicators of Sea Bass Semen Quality; Biology of Reproduction 70,1679-1684 (2004) Published online before print Feb. 11, 2004.

Hanania, E. G, et al. A novel Automated Method of Scanning Cytometry and Laser-Induced Necrosis Applied to Tumore Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce, E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

International Search Report, PCT/NZ98/00009; Jun. 16, 1998.

Bavister, B.D. et al., The effects of Sperm Extracts and Energy Sources on the Motility and Acromosome Reaction of hamster Spermatozoa in vitro; Biology of Reporduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

(Parent application) U.S. Appl. No. 11/536,492, filed Sep. 28, 2006, entire file wrapper available to USPTO examiner via PAIRS system.

Parallel Japanese Application No. 10-523769; Official action dated Mar. 13, 2007.

Parallel Australian Application No. 200503372; Official action dated Jan. 25, 2007.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 Dairy Sci 80:301-306.

Bagnato, A., Genetic and Breeding; Phenotypic Evaluation of Fertility Traits and Their Association with Milk Production of Italian Friesian Cattle; 1994 J. Diary Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Future—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Animals; Journal of Andrology, vol. 22, No. 4, Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fertilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (Anser anser L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18(2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffaloes (*Bubalus bubalis*) following deposition of sexed spermatozoa near the utero tubal junction, Reproduction in Domestic Animals, vol. 40, No. 1, Feb. 2005 , pp. 73-75(3).

Dielemann, S.J., Superovulation in cattle: from understanding the biological mechanisms to genomics of the oocyte; $23^{rd}$ Annual Meeting A.E.T.E.—Alghero; Sep. 2007.

Hasler, J. F., Factors influencing the success of embryo transfer in cattle; $23^{rd}$ World Buiatrics Congress, Quebec, Canada Jul. 2004.

Mapletoft, R. J. et al., Superovulation in perspective, Bioniche Animal Health, Dec. 2002.

Bahr, G.F.et al., Considerations of volume, mass, DNA, and arrangement of mitochondria in the midpiece of bull spermatozoa, Experimental Cell Research 60 (1970) 338-340.

Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.

BD LSR II Flow Cytometer, BD Biosciences Clontech Discovery labware Immunocytometry systems Pharmingen Jan. 28, 2004.

Bermudez, D.et al., The immediate effect of IR, laser radiation on rat, germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Sabuer K. et al."Effects of Angiotensin II on the Acrosome Reaction in Equine Spermatozoa" Journal of Reproduction and Fertility vol. 120, 2002 p. 135-142.

Brooks, D.E., Manipulation of Mammalian Gametes in Vitro, Biennial Report, Waite Agricultural Research Institute 1986-1989.

Bruemmer, J.E. et al., "Effects of Pyruvate on the Function of Stallion Spermatozoa Stored for up to 48 Hours", Journal of Animal Science 2002, vol. 80*1, pp. 12-18.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P., et al., Casein Kinase II activity and polyamine-stimulated protein phosphorylation of cytosolic and plasma membrane proteins in bovine sperm, Archives of Biochemistry and Biophyeics vol. 271, No. 1 pp. 98-106, May 15, 1989.

Chen, Y. et al., Effects of sucrose, trehalose, hypotaurine, taurine, and blood serum on survival of frozen bull sperm, Cryobiology 30,423-431 (1993).

Chapter 16 Semen processing, storage, thawing, and handling, http://nongae.gsnu.ac.kr/~cspark/teaching/chap16.html Sep. 23, 2002.

Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Graves, C.N., et al., "Metabolism of Pyruvate by Epididymal-Like Bovine Spermatozoa", 1964 Journal of Dairy Science vol. 47 (12), pp. 1407-1411.

Certified Semen Services, CSS Minimum requirements for disease control of semen produced for AI, http://www.naab-css.org/about_css/disease_control-2002.html Sep. 22, 2003.

Culling, "Handbook of Histopathological and Histochemical Techniques,"3rd Ed., Butterworths, pp. 192.

De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado,N. et al., Correlation between sperm membrane destabilization by heparin and aniline blue staining as membrane integrity index, Archives of Andrology40:147-152 (1998).

Denniston, D.J. et al., "Effect of Antioxidants on the Motility and Viability of Cooled Stallion Spermatozoa", Journal Reproduction Supplement 56, 2001, pp. 121-126.

De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Cho, et al. A microfluidic device for separating motile sperm from nomotile sprem via inter-streamline crossings.

Ericsson, R. et al., Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote,R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel,D.et al.,Flow cytometry of mammalian sperm progress in DNA and morphology measurement, The Journal of Histochemical and Cytochemistryvol. 27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of CO2-induced Inhibition of Mammalian Spermatozoa, 1959, Proc Soc Exp Biology Med, vol. 101 (1) pp. 187-189.

Centola, G.et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (Oncorhynchus mykiss)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Courtens, J. et al., Numerical simulation for freezing and thawing mammalian spermatozoa. Evaluation of cell injuries at different depths in bags or straws during all steps of the technique.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

Young, L.et al., Prolonged feeding of low levels of zearalenone to young boars.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 06, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al., Spermatozoa and Seminal Plasma, Reproduction in farm animals 7th edition.

Gadella B,et al., Dynamics in the membrane organization of the mammalian sperm cell and functionality in fertilization, Vet Quart. 21:142-146 (1999).

Garner, D.et al., Chromatin stability in sex-sorted sperm, VII International Congress of Andrology.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., "Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Guthrie, et al., "Flow Cytometric Sperm Sorting: Effects of Varying laser Power on Embryo Development in Swine", Mol. Reprod. And Develop., 2002,vol. 61 (1), pp. 87-92.

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2579 (1992).

Held, A.et al., Quasi- CW Solid- state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish AI bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement , Sep. 4, 1990.

Johnson, L., Flow sorting of intact X & Y chromosome-bearingmammalian spermatozoa, The Journal of the Society for Analytical Cytology Cytometry, (1988).

Zhang,M. et al., Development of bovine embryos after in vitro fertilization of oocytes with a flow cytometrically sorted, stained and unsorted sperm from different bulls, Theriogenology 60: 1657-1663 (2003).

Jones,R.et al., Effect of Osmolality and Phosphate, "Tris", "Tres", "Mes", nd "Herpes" Hydrogen ion buffers on the motility of bull spermatozoa stored at 37 or 5° C., Ausi J. Biol. Sci.25:1047-1055 (1972).

Jones,R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland.

Johnson, L., Separation of X and Y Chromosome-bearing mammalian sperm by DNA content cytometric analysis and sorting, US Department of Agriculture.

Johnson, M., The Macromolecular Organization of membranes and its bearing on events leading up to Fertilization, Journal of Reproduction and Fertility (1975).

Johnson, L., Verified Sex Pre-Selection in Farm Animals.

Johnson, L., Progress towards achieving sex preselection in farm animals, USDA Agricultural Research Service, (1989).

Kachel, V.et al., Uniform Lateral Orentation, caused by flow forces, of flat particles in flow-through systrms, The Journal of Histochemistry and Cytochemistry, vol. 25 No. 7 pp. 774-780 (1977).

Keeler, K.et al., Flow microfluorometric analysis of living spermatozoa stained with Hoechst 33342, J. Reprod.Fert. 68:205-212 (1983).

Keij, J.et al., High speed Photodamage cell sorting: An evaluation of the Zapper Prototype, Methods in cell Biology vol. 42, (1994).

Kirchhoff, C.et al., The Molecular biology of the sperm surface:Post-Testicular Membrane Remodelling, The Fate of the Male Germ Cell, (1997).

Krueger, C.et al.,Low dose Insemination in synchronized gilts, Theriogenology 52: 1363-1373 (1999).

Lahdetie,J.,Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J. et al., Orientation measurements of microsphere doublets and metaphase chromosomes in flow, Cytometry 7:575-581 (1986).

Luttmer, S. et al., Examination of living and fixed gametes and early embryos stained with supravital fluorochromes (Hoechst 33342 and 3,3'-dihexyloxacarocyanine Iodide), Gamete Research 15:267-283 (1986).

Masaki, J. et al., Effect of bull seminal plasma on the membrane characteristics of boarepididymal spermatozoa.

Maxwell, W. et al., Physiology of spermatozoa at high dilution rates: The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney, K. et al., Abstract: Insemination of lactating holstein cows with sexed frozen/thawed sperm, http://www.cvmbs.colostate.edu/physio/abstract/ges12.html Mar. 16, 2004.

Medeiros, C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M. et al., "Cytogenetic" studies of spermatids of mice carrying Cattanach's translocation by flor cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al., "Sexing of Sperm by Flow Cytometry", The Veterinary Record, 1988, pp. 322-324.

Morrier, A. et al., Glycerol addition and conservation of fresh and crypreserved ram spermatozoa, Canadian Journal of AnimalScience, Sep. 2002 http://pubs.nrc-cnrc.gc.ca/aic-journals/2002ab/cjas02/cjas02/cjas01-045.html.

Moruzzi, J., Selecting a mammalian species for the separation of X- and Y- chromosome- bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R&D Magazine, Dec. 2003: pp. 36-37 as currently presented on and printed from http://www.rdmag.com 2 pgs.

Gwo-Bin, L. et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983, pp. 11-19, 4, Allan R. Liss, Inc.

OcanaQuero, J. et al., Biological effects of helium-neon irradiation on acrosome reaction in bull, Scisearch Journal of Photochemistry and Photobiology, vol. 40 No. 3, pp. 294-299 (1997).

Pangawkar, G. et al., Physical and biochemical characteristics of semen in relation to fertility of Holstein-Friesian bulls, Indian vet. Med. J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R. et al., Semen plasma proteins prevent cold shock membrane damage to ram spermatozoa, Theriogenology 56 (3): 425-434, Aug. 1, 2001, PMID: 11516122 http://www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research An International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Polge, C., Low-temperature storage of mammalian spermatozoa, Unit of Reproductive Physiology and Biochemistry, Cambridge. Edited by Bell-Prince, C., NFCR Newsletter, http://www.ls.lanl.gov/NFCR/newsletter-Oc98/oct98.html Jan. 6, 2004.

Rasul, Z. et al., Changes in motion characteristics, plasma membrane integrity, and acrosome morphology during cryopreservation of buffalo spermatozoa, Journal of Andrology, vol. 22 No. 2, Mar.-Apr. 2001.

Rees, William A., et al, Betaine Can Eliminate the Base Pair Composition Dependence of DNA Melting; Biochemistry 1993, 32, pp. 137-144.

Rens, W. et al., An X-Y paint set and sperm FISH protocol that can be used for validation of cattle sperm separation procedures, Journals of Reproduction and Fertility, 121: 541-546 (2001).

Reyes-Mereno, C. et al., Characterization of Secretory Proteins from cultured Cauda Epididymal Cells that significantly sustain bovine sperm motility, Molecular Reproduction and Development 63: 500-509 (2002).

Rippel, N. et al., Transcervical insemination: Effects of variation in total sperm number/dose on fertility, 83rd Annual Fall Conference for Veterinarians, Oct. 2002.

Rizzo, W. et al., Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R. et al., Semen Quality test and their relationship to fertility, 4th National Association of Animal Breeders, (1972).

Salisbury, G.W., et al. "Preservation of Bovine Spermatozoa in Yolk-Citrate Diluent and Field Results from its Use", Journal of Dairy Science, 1941, vol. 24(11), pp. 905-910.

Schroter, S. et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online, vol. 7 No. 1 75-81, www.rbmonline.com/Article/847, Apr. 16, 2003.

Seidel, George E. Jr. "What about sexed semen?" Hoard's Dairyman, The National Diary Farm Magazine, May 10, 2001.

Sexing Technologies, Welcome to sexing Technologies, http://www.sexingtechnologies.com/ Dec. 11, 2003.

Shapiro, Howard M. M.D., Building Flow Cytometers Chapter 9. Practical Flow Cytometry, second edition, Property of Washington University Medical Library.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P. et al., Characteristics of a Novel Deep Red/Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J. et al., The Relationship between motility and the FITC-BSA binding Properties of Mouse epididymal spermatozoa, The Journal of Experimental Zoology 227: 323-327 (1983).

Stanic, P. et al., Comparison of protective media and freezing techniques for cryopreservation of human semen, http://www.ncbi.nlm.nih.gov/entrez/query.fcgi?CMD=search&DB=pubmed, Jul. 11, 2000.

Stewart, R., Georgia Beef Challenge, Livestock Newsletter Jan.-Feb. 2002.

Takacs, T.et al.,Flow Cytometric determination of the sperm cell number in diluted bull semen samples by DNA staining method, Acta Biochim.Biophys.Hung. vol. 22 No. 1, pp. 45-57 (1987).

Thurston,L. et al., Identification of Amplified restriction fragment length polymorphism markers linked to genes controlling boar sperm viability following cryopreservation, Biology Of Reproduction 66: 545-554 (2002).

Tone,S.et al., A method of vital staining of mouse eggs using Hoechst dye, Department of Developmential Biology (1986).

Tubman,L.eta l., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch, G.et al., Sex preselection: Laboratory Validation of the sperm sex ratio of Flow sorted X- and Y- sperm by sort reanal ysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during in vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.

XY, Inc., Sex selection Procedure, http://www.xyinc.com/sex select. html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Lindsey, A. C., et al., Hysteroscopic insemination of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1 . p. 369.

Palma, G. et al., Sperm Physiology: The Ability to Produce Embryos In Vitro using Semen from Bulls with a Low Non-Return Rate. Therio. p. 308.

Gottlinger, Christopher et al., Cell-Cooling in Flow Cytometry by Peltier Elements. Cytometry 7:295-297 (1986).

Abstracts: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.

Garner, Duane L., et al, Effect of Semen Dilution on Bovine Sperm Viability as Determined by Dual-DNA Straining and Flow Cytometry. J. or Andrology , vol. 18, No. 3 May/Jun. 1997.

Lindsey, A. L., et al., Hysteroscopic or rectally guided, deep-uterine insemination of mares with spermatozoa stored 18 h at either 5° C. or 15° C. prior to flow-cytometric sorting, Animal Reproduction Science, vol. 85, Issues 1-2, Jan. 2005, pp. 125-130.

Schenk, J. L., et al., Pregnancy rates in heifers and cows with cryopreserved sexed sperm: Effects of sperm numbers per inseminate, sorting pressure, and sperm storage before sorting, Theriogenology (2008), doi:10.1016/J. theriogenology. 2008:08:016.

Suh, T.K., et al., High pressure flow cytometric sorting damages sperm, Theriogenology 64 (2005) 1035-1048.

Upreti, G. C., et al., Studies on aromatic amino acid oxidase activity in ram spermatozoa: role of pyruvate as an antioxidant, Animal Reproduction Science 51 (1998) 275-287.

Schafer, D. J., et al., Comparison of progestin-based protocols to synchronize estrus and ovulation before fixed-time artificial insemination in postpartum beef cows, Journal of Animal Science Mar. 30, 2007, pp. 1-21.

Lamb, G. C., Synchronization of estrus and artificial insemination in replacement beef heifers using gonadotropin-releasing hormone, prostaglandin F2a and progesterone, Journal of Animal Science Nov. 1, 2006, vol. 84, pp. 3000-3009.

Saladarriage, J. P., Ovarian, hormonal, and reproductive events associated with synchronization of ovulation and timed appointment breeding in Bos indicus-influenced cattle using intravaginal progesterone, gonadotropin-releasing hormone, and prostaglandin F2a, Journal of Animal Science Jan. 2007, vol. 85, pp. 151-162.

O'Brien, J. K. et al., Semen collection, characterization an preservation in a beluga (*Delphinapterus leucas*), 1st International workshop on Beluga whale research, husbandry and management in wild and captive environments Mar. 2007.

O'Brien, J. K. et al., Development of sperm sexing and associated assisted reproductive technology for sex preselection of captive bottlenose dolphins (*Tursiops truncatus*), Reproduction, Fertility and Development 2008, 18, 319-329.

Parallel Australian application No. 2005203372, Letters Patent dated Oct. 2, 2008.

Parallel Japanese application No. 10/532763, Office action dated Aug. 14, 2008.

\* cited by examiner

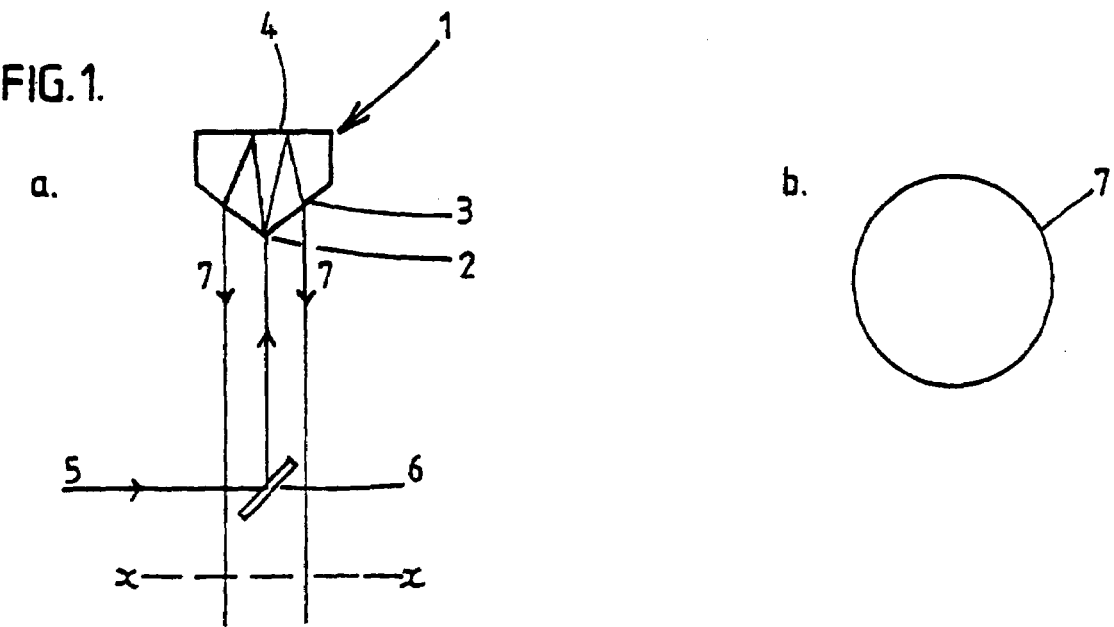
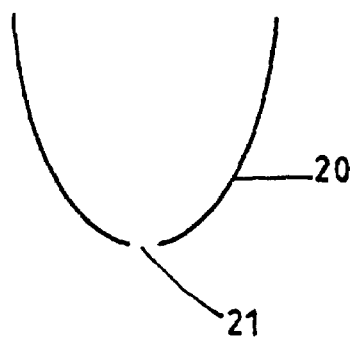

OPTICAL APPARATUS

This application is a divisional application of, and claims benefit of and priority to, U.S. patent application Ser. No. 10/990,648, filed Nov. 16, 2004, issuing May 22, 2007 as U.S. Pat. No. 7,221,453, which itself is a continuation application of, and claims the benefit and priority of, U.S. patent application Ser. No. 09/355,461, filed Sep. 17, 1999, issuing Nov. 16, 2004 as U.S. Pat. No. 6,819,411, which itself was a United States National Phase patent application of International Application No. PCT/NZ98/00009, published Aug. 6, 1998, filed Feb. 2, 1998, which itself claims the benefit of and priority of New Zealand Provisional Specification Number 314169 filed Jan. 31, 1997, each above-mentioned application hereby incorporated by reference.

BACKGROUND OF THE INVENTIVE TECHNOLOGY

This invention relates to an optical apparatus. In particular, although not exclusively, this invention has application to the field of flow cytometry. However, it is to be understood that several of the inventive aspects have application beyond flow cytometry and may have broad application in the field of optics generally. For example, several aspects of the invention may be used in photometry or optical particle detection apparatus.

Generally when illuminating a particle or an object for analysis, the light source is directed onto the particle from a single direction. An analysis may be made of light reflected or produced by the particle e.g. fluorescence to reveal certain properties of the particle. The particular portion of the particle illuminated depends on the orientation of the particle with respect to the light source. Where the particle or object is asymmetrical, the light measurements will vary depending on which portion is illuminated, making it difficult to analyze the particle or object as a whole.

Such difficulties are encountered in flow cytometry since it is common for particles being analyzed to be asymmetrical e.g. mammalian spermatozoa.

Flow cytometers are often used to measure the properties of cells or particles which are carried in a stream of fluid. The stream is generally comprised of a sheath fluid into the centre of which is injected a narrow aqueous suspension of cells/particles. The sheath fluid focuses the sample cells/particles into single file. The stream containing the particles/cells passes through an inspection point which is the focus of an intense light beam. The particles/cells may have been stained with a light-sensitive stain which when illuminated, will absorb the incident light and fluoresce. Light scatters off the particles and/or alternatively causes fluorescence. This scattered or fluorescent light is then measured by a detector generally aligned with the incident beam. The characteristics of the detected signal(s) such as peak intensity, peak area or other characteristics of interest may then be used to derive properties of the particle, for example size.

In a flow cytometer with sorting capability (as opposed to a purely analytical instrument) the detected signal(s) may be used to trigger sorting hardware which can be programmed to divert droplets from the stream of fluid. The sorting criteria will vary with the application, for example, the sorting may be conducted according to size or, in the case of spermatozoa, the DNA content of the cell.

One problem with conventional flow cytometers is that particle asymmetry often renders the optical characteristics of a particle difficult to measure. For example, a flat particle can pass through the inspection point with a random orientation. Thus, the intensity of the resultant scattered or fluorescent light may vary according to particle orientation and the detectors will measure different light intensities at different locations.

Thus, particle asymmetry can lead to a reduced resolution of measurement of the particles. It follows that, in cytometers with a sorting capability, this reduced resolution in measurement of the particles results in a decreased ability to accurately separate populations of cells with different optical properties. Such a problem is encountered in separation of male and female mammalian sperm.

In mammals, sperm carry the sex determining chromosomes and the total DNA content found in male and female sperm may differ. For example, in cattle the difference in the DNA content between male and female sperm is approximately 4%. This difference in DNA provides a means by which sperm may be separated in a sorting flow cytometer, making a predetermination of an offspring's sex possible when artificial breeding of animals is carried out. Utilizing such a technique in artificial breeding would offer considerable economic advantages in livestock management, but is currently made difficult by the asymmetric geometry of the flat sperm head. As an example, bull sperm are flat cells with head dimensions of approximately 10 microns by 4 microns by 1 micron attached to a 40 micron flagellum. The asymmetric properties of the bull sperm head result in a high variation in both scattered light and fluorescent light emission with sperm orientation. In particular, fluorescent emission varies by a factor of two with sperm orientation (see DNA Contention Measurements of Mammalian Sperm. CYTOMETRY 3:1-9 [1982]), effectively masking the 4% variation in intensity due to the sex of the sperm.

A number of flow cytometric systems have been developed in an attempt to overcome the problems encountered when analyzing asymmetric particles such as sperm cells.

One flow cytometric system that has been developed in an attempt to overcome this problem introduces asymmetric cells traveling in a slow moving stream into the middle of a fast flowing sheath stream. Hydrodynamics then tends to align the asymmetric cells with their long axis parallel to the direction of the fast flowing sheath stream.

While this approach tends to reduce the vertical variation of light intensity from asymmetric particles, the radial variation remains. This system has been further refined so as to further reduce the orientation-related variation in the detected light intensity of particles.

The system developed by Pinkel et al. (see Flow Cytometry in Mammalian Sperm. Progress Morphology and DNA Measurement. THE JOURNAL OF HISTOCHEMISTRY AND CYTOCHEMISTRY 24:353-358 [1979]), showed that the orientation of bull sperm could be further aligned by bevelling the end of the tube which injected the sample stream (i.e. that which contains the sperm) into the sheath flow.

The system which attempted to overcome the problems of flow cytometric analysis of asymmetric cells was that described by Johnson (see Sex Preselection by Flow Cytometric Separation of X AND Y Chromosome Bearing Sperm Based on DNA Difference: A review. REPRODUCTIVE FERTILITY DEVELOPMENTS 7:893-903 [1995]), in relation to separation of bull sperm by sex. Johnson's approach utilized two detectors; one in line with the illuminating laser beam (the 0 degree detector) and one at right angles to the beam (the 90 degree detector). Sperm emit fluorescence preferentially through their narrow edges. Johnson determined which sperm were aligned edge-on to the 90 degree detector by detecting the bright emission from their edges, and used the 0 degree detector for measuring the flat-face emission from only the aligned sperm.

However, this system still had a number of drawbacks. One drawback was that it was a requirement for this system that the sample flow be moving slowly with respect to the sheath flow, thereby reducing sample throughput. A further drawback was that it only produces good alignment at very low flow rates. At the optimal flow rate, which produced the greatest number of aligned cells per second, only 40% of cells were aligned. Thus, the number of aligned cells had been increased from 10% to 40%, but approximately 60% of the cells remained unaligned, and further, due to the requirement of a low flow rate, there was a reduction in system throughput.

It will be appreciated that the rejection of unaligned cells again reduces the processing rate of this system and unnecessarily wastes sperm cells.

One system which moved towards radial light collection was the Ellipsoidal Collector described by Skogen-Hagenson et al (see A High Efficiency Flow Cytometer, CYTOCHEMISTRY 25:784-789 [1977]), who developed a light collection system based on a hollow "egg shaped" brass reflector. The reflector surface was elliptical in cross-section and light from the inspection point at one focus was collected at the second focus. This system was demonstrated to have an ability to reduce the orientation dependence observed with bull sperm.

However, it still had orientation dependent illumination, (i.e. Light source coming from a single direction). A further problem with this system is that it is unable to provide a particle sort function (i.e. according to sperm sex).

A further system which implemented both symmetric illumination and symmetric light collection was the Epi-Illumination system described by Garner et al (see Quantification of the X and Y Chromosome Bearing Spermatozoa of Domestic Animals by Flow Cytometry, BIOLOGY OF REPRODUCTION 28:312-321 [1983]).

In this system the sample stream traveled directly towards a high numerical index microscope objective lens and was diverted sideways after the stream had passed through the focal point of the lens. Illumination was delivered through the lens and light was collected back through the lens.

While this system also demonstrated a good ability to eliminate the orientation dependencies of bull sperm, it was also incapable of modification for high speed sorting. This was due to its sideways diversion of the sperm immediately after passing through the focal point.

Earlier systems have also relied on laser light, because of the intensity of laser light sources. Unfortunately, such laser systems can be quite expensive and only add to the cost of devices such as flow cytometers. Because lasers typically deliver a single wavelength of light, use of lasers also has made it difficult to utilize a single light source to provide a variety of wavelengths of light, e.g. in conjunction with filters that filter out all but the desired wavelengths.

Furthermore, previous systems have often required the precise alignment of optics in order to accomplish a proper delivery of electromagnetic radiation onto the cell under analyzation or collection of fluorescence emitted by a cell. This can be a tedious process that adds to the expense of the analyzation instruments. Hence, there is a need for a system, e.g., in flow cytometry, in which the optics that focus and collect electromagnetic radiation for measurement purposes are quickly and easily established in their proper orientation.

It is an object of the present invention to overcome the afore mentioned shortcomings of known optical apparatus with particular application to flow cytometers. It is also an object of the invention to provide the public with a useful choice.

SUMMARY OF THE INVENTION

In accordance with a first aspect of the present invention there is provided an optical apparatus including: a prism having a conical portion with an apex at a forward end of the prism and a central axis extending through the apex of the prism; an optical arrangement including a source of electromagnetic radiation, the optical arrangement adapted to direct an incident beam of electromagnetic radiation onto the apex of the conical portion in a direction substantially aligned with the central axis of the conical portion; and a reflective surface provided behind the apex of the prism; such that the beam refracted by the prism will be reflected by the reflective surface back through the prism to project from the forward end of the prism as an annular beam of electromagnetic radiation.

The optical apparatus described above thereby serves to produce an annular beam of electromagnetic radiation from a single beam of electromagnetic radiation incident onto the apex of the conical portion. Preferably, the arrangement is such to provide the beam with a constant cross section to produce a cylindrical tube of light. The prism may also include a cylindrical base portion at a rear end thereof which has a circular cross section corresponding to the cross section of the base of the conical portion.

In accordance with a second aspect of the present invention there is provided an optical apparatus including: a prism having a pyramidal portion with an even number of inclined faces meeting at an apex at a forward end of the prism and a central axis extending through the apex an optical arrangement including a source of electromagnetic radiation, the optical arrangement adapted to direct an incident beam of electromagnetic radiation onto the apex of the pyramidal portion in a direction substantially aligned with the central axis of the pyramidal portion; and a reflective surface provided behind the apex of the prism; such that the beam refracted by the prism will be reflected by the reflective surface back through the prism to project from the forward end of the prism as a number of parallel beams.

It is required that the pyramidal portion have an even number of inclined faces since the optical geometry is such that the beams cross the prism to reflect from the opposing face. Apart from this constraint, the number of the inclined faces is not limited. For example, there may be 4, 6, 8 . . . 12 inclined triangular faces converging towards the apex of the pyramidal portion. Preferably, the pyramidal portion also includes a base portion with a cross section corresponding to the base of the pyramidal portion. For example, where the pyramid has four inclined faces an appropriate base portion would be a rectangular prism or a cube.

In either of the first two aspects of the invention, the reflective surface may be provided at the rear end of the prism. However, the invention is not limited to this arrangement and may potentially be disposed within the prism itself. Another preferred arrangement is for the reflective surface to be spaced from the base portion. Another desirable feature is that this spacing be adjustable to provide a variable annular beam diameter.

However, where the reflective surface is spaced from the prism the electromagnetic radiation may suffer losses from multiple interface reflection. However, as such a design would have a reduced length from the front to the rear end, the transmission losses would be less than for a longer prism with the reflective surface provided at the rear end.

Suitably the prisms are manufactured from optical glass such as BK7 optical glass. However, where the application is intended for use with UV electromagnetic radiation, it is preferred to manufacture the prism from UV-suitable material such as fused silica. In such an application, it is also desirable that the reflective surface be comprised of a UV-grade mirror to increase the transmission efficiency of the optical apparatus.

As mentioned above, the optical apparatus may be used with ultra-violet radiation, preferably produced from a laser source. The electromagnetic radiation may also include other wavelengths including those in the visible spectrum. Suitably, the incident electromagnetic radiation is in the form of a collimated beam.

The optical apparatus described above in connection with the first two aspects may desirably be used in combination with a paraboloid reflector having an internal paraboloidal-shaped reflective surface and an optical axis. Such a reflector will be oriented to receive, on its reflective surface, the electromagnetic radiation projected from the forward end of the prism. It will be appreciated that such a paraboloidal-shaped reflective surface will have a focus at which all light parallel to the optical axis and incident onto the reflective surface will be directed. In other words, the parallel electromagnetic radiation projected from the prism will be received onto the paraboloid reflector to converge at the focus. Such a concentration of electromagnetic radiation may have many useful and varied applications in the field of optics. In particular, the invention is capable of providing radially symmetric illumination to the focus of the paraboloid reflector. The term "radially symmetric" means that for every beam of incident radiation to the focus, a substantially diametrically opposite beam will be incident to the focus. Each beam of the radially symmetric illumination may have the same angle to the optical axis of the paraboloid reflector. Thus a convergent disc of electromagnetic radiation onto the focus will be included in the definition of "radially symmetric". Such a convergent disc can be achieved through the use of the first-described optical apparatus in combination with the paraboloid reflector. Any object can be placed at the focus of the paraboloid reflector for illumination and inspection. As will be discussed with following aspects of the invention, the apparatus has particular application to flow cytometry in that a flow source may be provided to direct particles through the focus of the paraboloid reflector.

It will be understood that the source of electromagnetic radiation may not be directed directly at the apex of the prism and the invention allows for the use of mirrors and other reflectors as desired. In particular, a second reflector may be disposed between the prism and the paraboloid reflector, the second reflector having reflective portions to reflect the incident beam from the source onto the apex of the prism and transmitting portions to transmit the beam(s) projected from the forward end of the prism.

However, the invention is not limited to the particular prisms described in the forgoing aspects of the invention. Other optical configurations are envisaged to produce the projected annular beam or parallel beams of electromagnetic radiation. Furthermore, other types of reflectors which focus incident radiation towards one or more foci could be adopted.

Accordingly, a third aspect of the invention provides an optical apparatus including an optical configuration adapted to produce an annular beam of electromagnetic radiation having a central axis or plurality of beams of electromagnetic radiation wherein said plurality of beams are evenly spaced from a central axis; and a focusing reflector having an internal reflective surface having an optical axis and one or more foci, the reflector being oriented to receive, onto its reflective surface, the annular beam or the plurality of beams of electromagnetic radiation.

For example, the optical element may comprise any known reflective axicons as well as the particular prisms described above which, in some cases are also axicons. For example, the axicon may comprise an inner conical mirror with forward reflective surfaces surrounded by an outer conical mirror with forward reflective surfaces wherein the optical axes of the two mirrors are aligned. The reflective surfaces form the letter "W", hence the name w-axicon or waxicon.

Preferably, the focusing reflector has an internal reflective surface which is paraboloid in shape. The use of the term "paraboloid reflector" used throughout the specification and the claims will be understood to mean "a reflector conforming to the shape of a paraboloid of revolution". The term is also to be understood to mean "a portion of a full paraboloid of revolution". Similarly, in regard to the optical axis of a paraboloid, such an axis may also be considered to be the parabolic or central axis of the paraboloid.

As mentioned in connection with the foregoing aspect of the invention, the apparatus may be incorporated into a flow cytometer including a flow source to produce a flow of particles to be analyzed in which the flow source is adapted to direct the flow of particles substantially through one of the foci of the reflective surface. Suitably the flow source can be adapted to substantially align the flow with the optical axis of the reflective surface. Moreover, an aperture may be provided in the focusing reflector for passage of the flow therebeyond.

It is desirable that the present invention will be used in a flow cytometer accommodating a sorting function. Thus, the flow means may include a nozzle and the flow cytometer may incorporate electrostatic droplet deflection sorting apparatus below the aperture in the focusing reflector.

In accordance with a fourth aspect of the present invention there is provided an optical method including: providing a prism having a conical portion with an apex at the forward end, a central axis extending through the apex and a reflective surface provided behind the apex of the prism; directing an incident beam of electromagnetic radiation onto the apex of the conical portion in a direction substantially aligned with the central axis of the conical portion to produce an annular beam of electromagnetic radiation projecting from the forward end of the prism.

In accordance with a fifth aspect of the present invention there is provided an optical method including: providing a prism having a pyramidal portion with an even number of inclined faces meeting at an apex at a forward end of the prism, a central axis extending through the apex and a reflective surface provided behind the apex of the prism; directing an incident beam of electromagnetic radiation onto the apex of the pyramidal portion in a direction substantially aligned with the central axis of the pyramidal portion to produce parallel beams of electromagnetic radiation projecting from the forward end of the prism.

In accordance with another aspect of the present invention there is provided an analyzation instrument including: a flow source to produce a flow of particles to be analyzed, the flow source being adapted to direct the flow of particles through an inspection zone; an optical arrangement including a source of electromagnetic radiation, the optical arrangement adapted to converge substantially coplanar, substantially radially symmetric electromagnetic radiation towards the inspection zone.

Preferably, the electromagnetic radiation coverges in the form of a disc disposed symmetrically relative to the central axis.

In accordance with yet another aspect of the present invention there is provided a method of analyzing including: providing a flow of particles to be analyzed; directing the flow of particles to be analyzed through an inspection zone; converging substantially coplanar, substantially radially symmetric electromagnetic radiation towards the inspection zone.

In accordance with a further aspect of the present invention there is provided an analyzation instrument including: a flow source to produce a flow of particles to be analyzed; a source of electromagnetic radiation; a reflector adapted to reflect at least a portion of the electromagnetic radiation at the flow of particles to illuminate the flow of particles; an optical configuration including a sensor adapted to sense electromagnetic radiation; wherein the reflector is also adapted to reflect, to the optical configuration, any electromagnetic radiation produced as a result of the illumination of the flow of particles.

Thus the reflector described in accordance with this aspect serves the dual purpose of reflecting the electromagnetic radiation onto the flow of particles as well as collecting the electromagnetic radiation for transmission to the sensor. Such a configuration can be achieved with the use of a reflector having an internal reflective surface which is paraboloid in shape.

It will be understood that any use of the term "illumination" or "illuminate" is not restricted to merely visible illumination as non-visible wavelengths may also be used. As mentioned previously, in certain applications ultra violet radiation may be used. Furthermore, reference to electromagnetic radiation "produced" by the particle may include any florescence produced by the particles as a result of the incident illumination and/or any light scattered by the particles. It should also be understood that "irradiate" is intended to have the same meaning as "illuminate".

In accordance with a still further aspect of the present invention there is provided a method of analyzing including providing: a flow of particles to be analyzed; providing a source of electromagnetic radiation; reflecting with a reflector at least a portion of the electromagnetic radiation to illuminate the flow of particles; reflecting with the reflector at least a portion of any electromagnetic radiation produced from the illumination of the flow of particles; sensing a portion of the electromagnetic radiation produced from the illumination of the flow of particles.

In accordance with still a further aspect of the present invention there is provided a flow cytometer including: a flow source to produce a linear flow of particles to be analyzed, the flow source being adapted to direct the flow of particles through an inspection zone; an optical arrangement adapted to converge electromagnetic radiation onto the flow at the inspection zone in a radially symmetric manner about the inspection zone; a collector to collect electromagnetic radiation either produced or deflected from the particles in the flow; a processor to derive, from the collected electromagnetic radiation, predetermined information relating to each of at least some of the particles in the flow; and a correlator to correlate the derived information with the associated particle downstream of the inspection zone.

As mentioned previously, the radially symmetric illumination may be provided in the form of a continuous disc convergent towards the inspection zone. Another preferred radially symmetric arrangement of the illumination is in the form of discreet beams converging towards the inspection zone. Either way, the particle is illuminated evenly from all sides.

In accordance with a further aspect of the present invention there is provided a flow cytometer including: a flow source to produce a linear flow of particles to be analyzed, the flow source being adapted to direct the flow of particles through an inspection zone; and an optical arrangement including a focusing reflector having an internal reflective surface with one or more foci, the optical arrangement adapted to converge electromagnetic radiation onto the flow of particles at the inspection zone by reflection from the focusing reflector, the focusing reflector being oriented such that one of the one or more foci is substantially coincident with or located within the inspection zone.

Various embodiments of the focusing reflector have been envisaged. In one such embodiment the focusing reflector comprises a paraboloid reflector having an internal reflective surface of paraboloidal-shape. The flow of particles will thus flow through the focus of the paraboloid reflector at which the electromagnetic radiation is converged. In another embodiment of the invention the focusing reflector may have an ellipsoidal reflective surface with two foci and an optical axis extending between the two foci. In particularly preferred versions of this, the flow source is oriented so that the flow of particles is aligned with the optical axis of the reflective surface. Moreover, any forms of the focusing reflector may be provided with an aperture for the passage of flow beyond the focusing reflector. Such an embodiment is particularly adapted for use in a sorting flow cytometer which collects the electromagnetic radiation produced from the particles in the flow, processes the collected electromagnetic radiation to derive predetermined information relating to each of at least some of the particles in the flow and correlates the derived information with the associated particle downstream of the inspection zone. In this way, the sorting flow cytometer can not only analyze the particles in the flow but sort the particles according to predetermined sets of selection criteria. A preferred type of sorting flow cytometer is a jet-in-air flow cytometer.

In another aspect of the present invention there is provided a flow cytometer including: a flow source to produce a flow of particles to be analyzed, the flow source being adapted to direct the flow of particles through an inspection zone; an optical arrangement including a source of electromagnetic radiation, the optical arrangement adapted to direct electromagnetic radiation onto the flow of particles, at the inspection zone; a collector to collect electromagnetic radiation either produced or deflected from the particles, the collector having an internal reflective surface with an optical axis and one or more foci, wherein the collector is oriented such that the flow of particles is substantially aligned with the optical axis.

In yet another aspect of the present invention there is provided a flow cytometer including: a flow source to produce a flow of particles to be analyzed, the flow source being adapted to direct the flow of particles through an inspection zone; an optical arrangement including a source of electromagnetic radiation, the optical arrangement adapted to direct electromagnetic radiation onto the flow of particles, at the inspection zone; a collector to collect electromagnetic radiation either produced or deflected from the particles, the collector having an internal reflective surface with an optical axis and one or more foci, wherein the collector is disposed such that one of the one or more foci is substantially coincident or located within the inspection zone; a processor to derive, from the collected electromagnetic radiation, predetermined information relating to each of at least some of the particles in the flow; and a correlator to correlate the derived information with the associated particle downstream of the inspection zone.

The collector may be of the same form as the focusing reflector as described in accordance with previous aspects of the invention. In fact, the collector may also comprise part of the optical arrangement adapted to direct electromagnetic radiation onto the flow of particles. In other words the collector may serve the dual function of collecting the produced electromagnetic radiation as well as reflecting the incident radiation onto the particles.

In accordance with another aspect of the present invention there is provided an analyzation instrument including: a first reflector having a partial ellipsoidal shape; a near focal point of the partial ellipsoidal shape of the first reflector; a distant focal point of the partial ellipsoidal shape of the first reflector; a central axis of the partial ellipsoidal shape defined by the near focal point and distant focal point of the partial ellipsoidal shape of the first reflector; a source of electromagnetic radiation disposed at the near focal point of the partial ellipsoidal shape capable of emitting electromagnetic radiation toward the first reflector; a second reflector having a partial ellipsoidal shape oriented relative to the first reflector so as to be capable of receiving electromagnetic radiation reflected by the first reflector; a near focal point of the partial ellipsoidal shape of the second reflector; a distant focal point of the partial ellipsoidal shape of the second reflector; a central axis of the partial ellipsoidal shape defined by the near focal point and distant focal point of the partial ellipsoidal shape of the second reflector; a flow source to produce a flow of particles to be analyzed; and an inspection zone of the flow of particles located at the near focal point of the partial ellipsoidal shape of the second reflector.

In a preferred embodiment, the source of electromagnetic radiation may comprise an arc lamp. Further, a preferred relationship between the first reflector and the second reflector is that the distant focal point of the first reflector and the distant focal point of the second reflector overlap. The focal lengths of the first and second reflectors may be equivalent. Alternatively, the focal lengths of the two reflectors may be different in that the first reflector has a greater focal length than the second reflector.

The term "ellipsoidal reflector" as used in the above described aspect of the invention and in following aspects and in the following description of the invention, is understood to mean a reflector which conforms to the shape of an ellipsoid of revolution. Furthermore, the term is understood to mean a portion of a full ellipsoid of revolution such as one third of an ellipsoid of revolution with an opening at the vertex.

In referring to ellipsoids throughout this description where only a partial ellipsoid is used, the near focal point is intended to mean the focal point closest to the ellipsoidal portion being used.

In accordance with yet another aspect of the present invention there is provided a method of analyzing including: utilizing a first reflector having a partial ellipsoidal surface with a near focal point and a distant focal point; emitting electromagnetic radiation from a source of electromagnetic radiation positioned at the near focal point of the first reflector; reflecting electromagnetic radiation emitted by the source of electromagnetic radiation from the first reflector; utilizing a second reflector having a partial ellipsoidal surface with a near focal point and a distant focal point; providing a flow of particles to be analyzed; directing the flow of particles through an inspection zone; positioning the second reflector so that the near focal point of the second reflector overlaps the inspection zone and so that the second reflector is capable of receiving electromagnetic radiation reflected by the first reflector.

In accordance with another object of the present invention there is provided an analyzation instrument including: a first reflector having a partial paraboloid shape; a focal point, and a focal length of the partial paraboloid shape of the first reflector; a parabolic axis of the partial paraboloid shape of the first reflector; a source of electromagnetic radiation disposed at the focal point of the partial paraboloid shape adapted to emit electromagnetic radiation toward the first reflector; a second reflector having a partial paraboloid shape oriented relative to the first reflector so as to be capable of receiving electromagnetic radiation reflected by the first reflector; a focal point, and a focal length of the partial paraboloid shape of the second reflector; a parabolic axis of the partial paraboloid shape of the second reflector; a flow source to produce a flow of particles to be analyzed; and an inspection zone of the flow of particles located at the focal point of the partial paraboloid shape of the second reflector.

An arc lamp may be the source of electromagnetic radiation. It is preferred that the parabolic axes, i.e., optical axes, of the first and second shapes-shapes are colinear. In one embodiment of the invention the focal lengths of the first and second reflectors may be equivalent. Alternatively the focal length of the first reflector may be greater than the focal length of the second reflector. A filter may be arranged between the focal points of the two reflectors.

In another aspect of the present invention there is provided a method of analyzing including: utilizing a first reflector having a partial paraboloid surface, an optical axis and a focal point; emitting electromagnetic radiation from a source of electromagnetic radiation positioned at the focal point of the first reflector; reflecting electromagnetic radiation emitted by the source of electromagnetic radiation from the first reflector; utilizing a second reflector having a partial paraboloid surface, an optical axis and a focal point; providing a flow of particles to be analyzed; directing the flow of particles through an inspection zone; positioning the second reflector so that the focal point of the second reflector overlaps the inspection zone and so that the second reflector is capable of receiving electromagnetic radiation reflected by the first reflector.

The present invention also provides, in accordance with another aspect of the invention, a nozzle including an opening for a flow of particles to flow through; a reflector coupled to the nozzle and oriented to reflect electromagnetic radiation at the flow of particles.

The reflector may take on various forms such as an ellipsoidal reflective surface or a paraboloid reflective surface, the reflector and the nozzle may even be integral. In a preferred embodiment of the invention, the flow of particles passes through an inspection zone and a source of electromagnetic radiation is provided to illuminate the inspection zone. Where the reflective surface is of the kind having a focal point, then it is preferred that the focal point of the reflective surface overlaps the inspection zone.

In preferred forms of the invention, the reflective surface may comprise a metal shape embedded in the nozzle. Alternatively, the reflective surface may comprise a reflective coating applied to the nozzle. Suitably, the focal point of the reflective surface can be external to the nozzle. The nozzle may be adapted to receive electromagnetic radiation through the opening in the nozzle to illuminate the reflector or through the nozzle material itself, e.g. via light transmission through a glass nozzle.

In accordance with a further aspect of the invention there is provided a method of illuminating a flow of particles, the method including: providing a nozzle having a reflector coupled to the nozzle and oriented to reflect electromagnetic radiation; supplying a flow of particles; directing the flow of particles through the nozzle; reflecting electromagnetic radiation with the reflector toward the flow of particles.

Another aspect of the invention provides a flow cytometer including: a flow source to produce a flow of particles to be analyzed, the flow source being adapted to direct the flow of particles through an inspection zone; an optical arrangement including a source of electromagnetic radiation, the optical arrangement adapted to direct electromagnetic radiation onto the flow of particles, at the inspection zone; a partial ellipsoidal collector to collect electromagnetic radiation either produced or deflected from the particles, the collector having an internal reflective surface of partial ellipsoidal shape with two foci and an optical axis oriented along a line between the two foci; the flow source being oriented such that the flow of particles is substantially aligned with the optical axis.

The preferred form of the flow cytometer may be a jet-in-air flow cytometer. Most preferably, the flow cytometer enables sorting through the use of electrostatic plates.

A corresponding aspect of the invention provides a method of flow cytometry including passing a flow of particles to be analyzed through an inspection zone; providing a focusing reflector having one or more foci; converging electromagnetic radiation onto the flow of particles at the inspection zone by reflection from the focusing reflector and aligning the inspection zone with one of the one or more foci.

BRIEF DESCRIPTION OF DRAWINGS

Further aspects of the present invention will become apparent from the following description which is given by way of example only and with reference to the accompanying drawings in which.

FIG. 1(a) is a cross-sectional view of one embodiment of an optical apparatus capable of producing an annular beam of electromagnetic radiation;

FIG. 1(b) is a section through the beam of FIG. 1;

FIG. 2 is sectional view of a paraboloid reflector;

DETAILED DESCRIPTION OF THE PREFERRED EMBODIMENTS

Figure 1D:
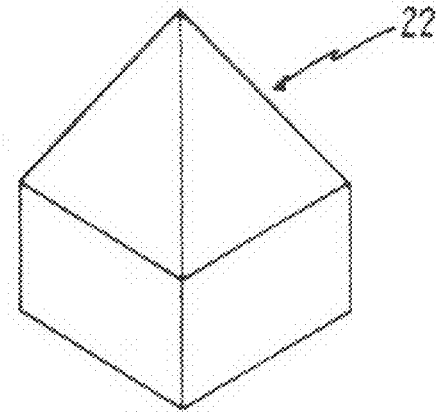
FIG. 1(d) is a perspective view of one embodiment of a prism for use in the optical apparatus of FIG. 1(a)

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Some embodiments of the invention are discussed in "A New Optical Configuration for Flow Cytometric Sorting of Aspherical Cells", Int. Soc. Optical Engr., Proc. Of Adv. Tech. Analytical Cytology, 1997, by John C. Sharpe, Peter N. Schaare and Rainer Kunnemeyer; "Radially Symmetric Excitation and Collection Optics for Flow Cytometric Sorting of Aspherical Cells", Cytometry 29:363-370 (1997) by John C. Sharpe, Peter N. Schaare, and Rainer Kunnemeyer; and "A New Optical Configuration for Flow Cytometric Sorting of Bovine Spermatozoa by Sex", a thesis submitted to the University of Waikato for the degree of Doctor of Philosophy in Physics by Johnathan Charles Sharpe, which are hereby incorporated by reference.

FIG. 1(a) illustrates an optical apparatus including a prism 1. The prism 1 has an apex 2 at a forward end of the prism, a right conical portion having a conical face 2, and a right cylindrical base portion contiguous with the conical portion. The base portion has a circular shaped rear end 4 with a reflective coating. An optical arrangement is provided to provide incoming electromagnetic radiation 5 such as ultra-violet light from a laser light source. The UV light 5 is directed in direction aligned with the central axis of the prism 1 onto the apex 2 of the prism 1 via a second reflector in the form of mirror 6 positioned at an angle of 45 degrees with respect to the incoming light 5 and the central axis of the prism 1. As the incoming light 5 enters the prism 1 via the apex 2 it is refracted by the prism 1 and diverges in a cone and is reflected off the rear end 4 of the lens 1. The reflected light exits the prism 1 through its conical face 3 and is projected from the forward end of the prism as an annular beam. The beam defines an enclosed cylindrical band of light having a longitudinal axis coincident with the central axis of the prism 1. FIG. 1(b) shows a cross section through the enclosed band of light. The production of a cylindrical band of light may have many uses throughout the field of optics. FIG. 1(e) illustrates the prism 1 in perspective view.

Figure 1E:
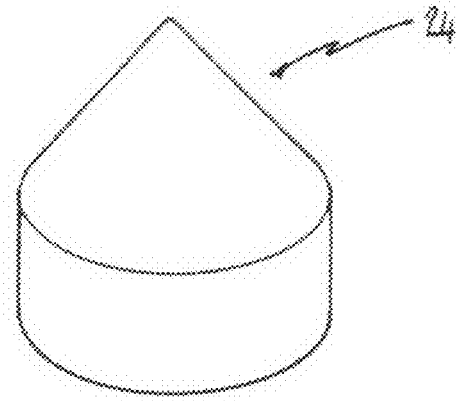
FIG. 1(e) is a perspective view of an alternative form of a prism for use in the optical apparatus of FIG. 1(a)

FIG. 1(d) illustrates an alternative form of prism 22. The prism 22 has a right pyramidal portion with four inclined faces meeting at an apex. A base portion is also provided which is square in cross-section, corresponding to the cross-section of the base of the pyramidal portion. The prism can be used in the same manner as prism 1 by directing incident light onto the apex of the prism in line with the central axis of the prism. However, in this embodiment, the projected light will emerge as four parallel beams equally spaced from the central axis. The number of inclined faces of the pyramidal portion may vary, provided that an even number is maintained.

Figure 1F:
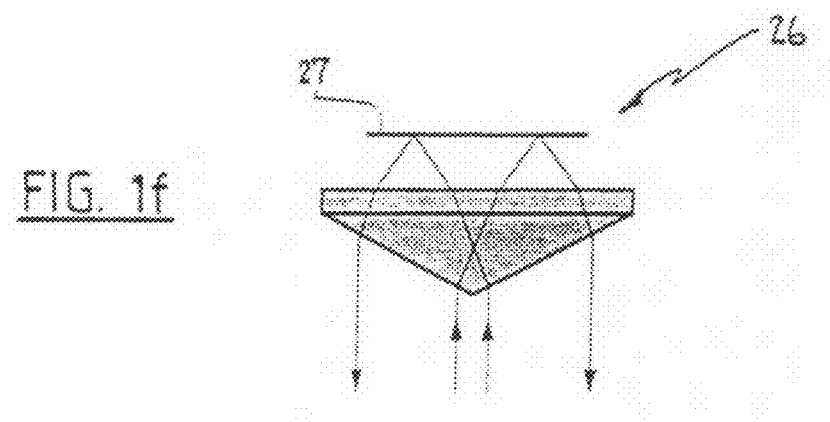
FIG. 1(f) is a perspective view of an alternative prism arrangement for use in the optical apparatus of FIG. 1(a)

FIG. 1(f) illustrates an alternative prism arrangement in which a reflective surface may be spaced from the rear end of the conical prism shown in FIG. 1(e) or the pyramidal prism shown in FIG. 1(d). The spacing of the reflective surface 27 from the prism may be adjustable.

Figure 1G:
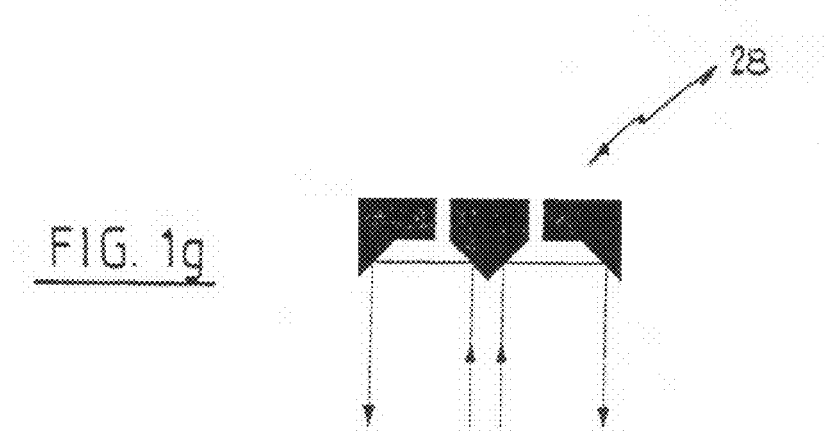
FIG. 1(g) is a perspective view of an alternative prism arrangement for use in the optical apparatus of FIG. 1(a)

FIG. 1(g) illustrates an alternative prism arrangement known as a w-axicon or waxicon. The waxicon 28 comprises an inner conical axicon surrounded by an annular axicon concentric with the inner axicon. The reflective surfaces define a W, hence the name waxicon.

FIG. 2 shows a paraboloid reflector 20 in the form of a mirror having a paraboloidal-shaped internal reflective surface. The paraboloid internal reflective surface has a focus and an optical axis running through the focus. It will be understood that the paraboloid shaped reflective surface can have the property whereby any light which leaves the focus of the paraboloid reflector and becomes incident on the surface of the reflector will be reflected out of the reflector 20 parallel to the optical axis. Likewise, when light which is reflected parallel to the optical axis enters and hits the reflective surface, it will be projected toward and through the focus. An aperture 21 is centrally positioned within the paraboloid reflector 20, in line with the optical axis.

Thus, the paraboloid reflector 20 may be used to provide multi-directional illumination of an object for analysis or inspection. By positioning the object at the focus of the paraboloid reflector 20 and providing light incident on the surface of the reflector 20 and parallel to the optical axis of the reflector 20, the incident light can be reflected towards the object at the focus. Further, if the incoming parallel light is evenly spaced in relation to the optical axis then the light illuminating the object at the focus will be radially symmetric. The paraboloid reflector 20 may thus be teamed with the optical apparatus shown in FIG. 1 in a manner in which the paraboloid reflector 20 is oriented to receive the light projected from the forward end of the prism 1 with the central axis of the prism 1 aligned with the optical axis of the paraboloid reflector 20. This particular arrangement is discussed further in connection with the flow cytometer shown in FIGS. 6, 7, 9, 10, 11, 13. However the paraboloid reflector is not limited in its use in combination with the optical apparatus shown in FIG. 1.

Figure 3:
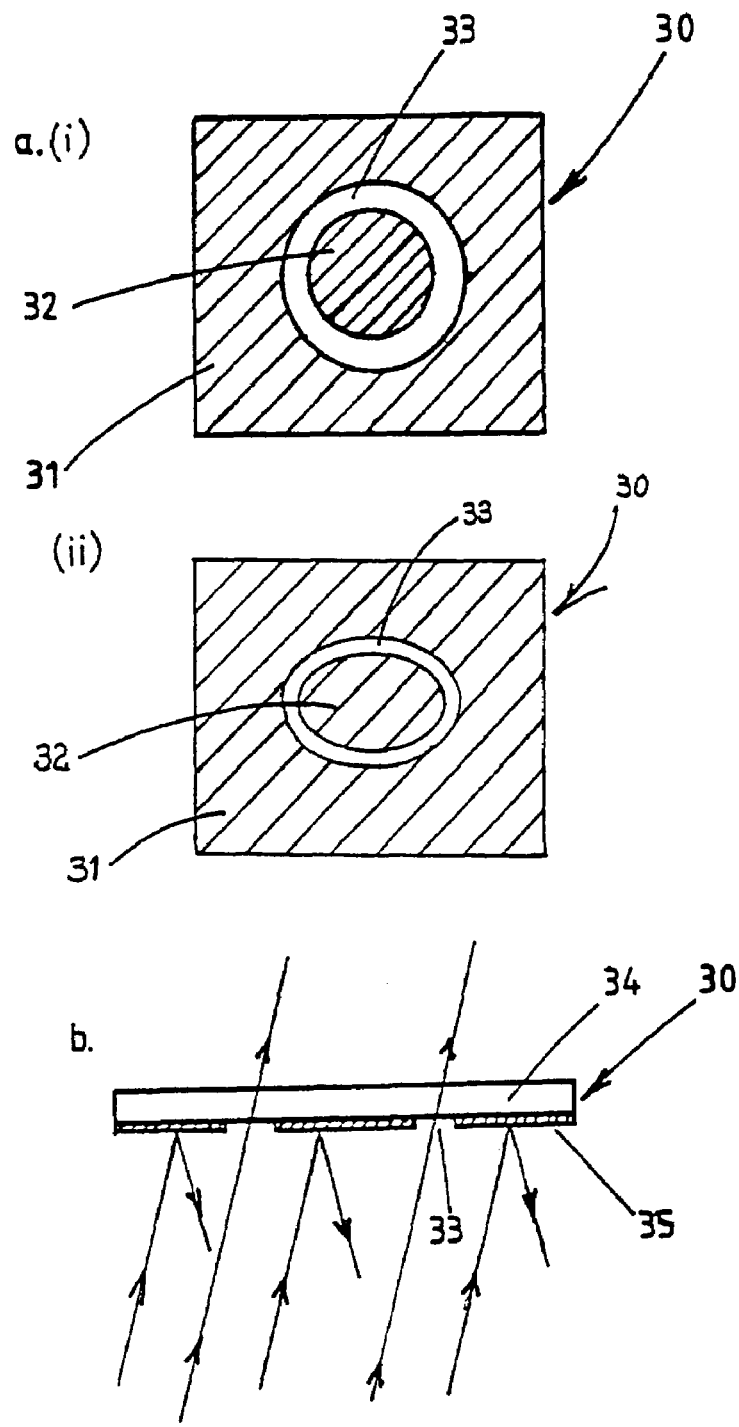
FIG. 3 shows various views though a reflector which includes transmitting and reflecting surfaces.

FIG. 3(a) (i) and (ii) are plan views of another embodiment of the second reflector of FIG. 1 generally indicated by arrow 30. The mirror 30 includes reflective surfaces 31 and 32. The mirror 30 also includes a transmitting portion which is in the form of an annular ring 33. It should be appreciated that in some embodiments the transmitting portion 33 may be in the form of an aperture which extends through the mirror 30. However, in other embodiments such as that shown more clearly in FIG. 3(b), the transmitting portion 33 may be in the form of a transparent material, such as glass 34 which has not been covered by a reflective surface 35. As FIG. 3(b) shows, any incoming light 36 that impacts on the reflective surface 35 is reflected, whereas incoming light which impacts on the transmitting portion 33 may continue to travel substantially in the same direction The transmitting portion 33 when arranged at a 45 degree angle from which it is viewed in plan in FIG. 3(a) (i) serves to allow passage of the annular beam of light projected from the forward end of the prism. FIG. 3(a) (ii) shows a plan view of the second reflector having an egg-shaped transmitting portion 33 necessary to achieve the annular transmitting portion 33 when oriented at 45 degrees.

Figure 4:
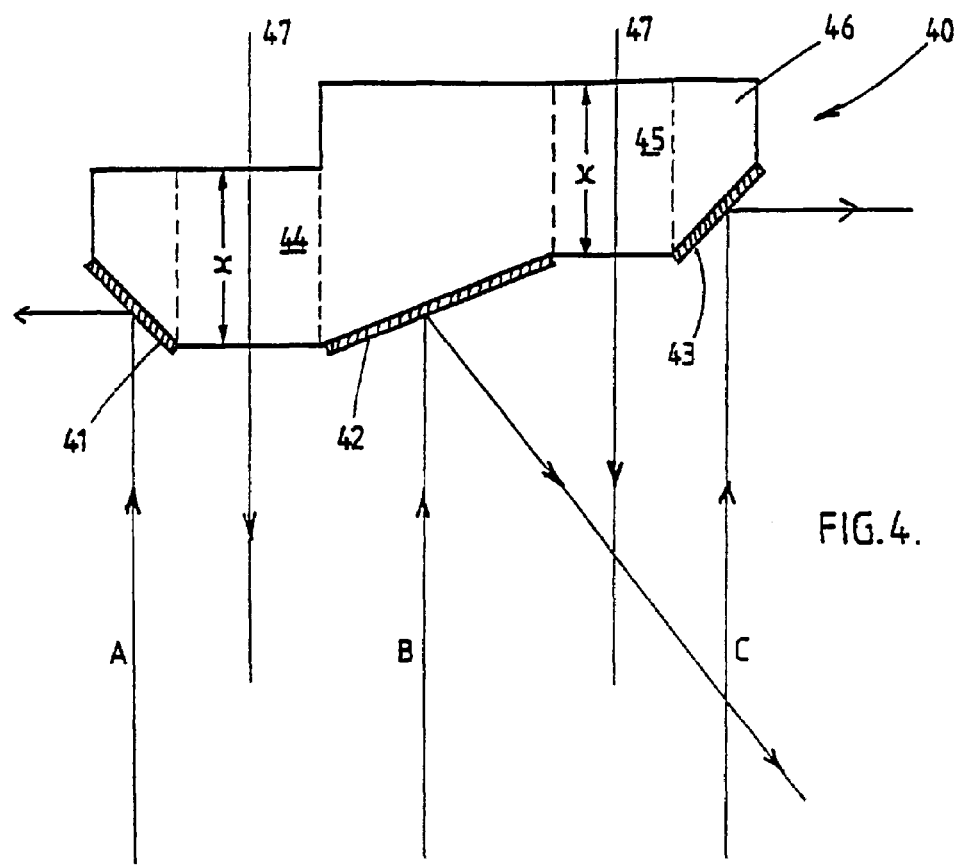
FIG. 4 is a cross-sectional view of a possible embodiment for a reflector apparatus.

FIG. 4 shows an alternative reflector apparatus generally indicated by arrow 40 which may be used to collect illumination reflected from the paraboloid reflector 20 in FIG. 2. The reflector apparatus 40 includes a body 46 having a number of reflective surfaces 41, 42 and 43 which are positioned with respect to the detector apparatus 40 so that they may reflect any light they receive in different directions and/or at different angles.

The reflector apparatus 40 also includes within its body 46 regions 44 and 45 (both of which are bounded by dotted lines) which allow for the transmission of light 47 through the reflector apparatus 40. It should be appreciated that the regions 44 and 45 may be in the form of apertures through the body 46 or alternatively made of a transparent substance/material capable of allowing for the transmission of light. In embodiments where regions 44 and 45 are made of a transparent substance/material it will usually be desirable that the regions have the same length as shown by double headed arrow x to ensure distance traveled and refraction of the light 47 is substantially identical in both regions.

The reflective surfaces 41, 42, and 43 are capable of discriminating against the different types of light A, B and C that may be received by the reflector apparatus 40, by reflecting it in different directions and/or at different angles. Thus, the different types of light A, B and C may be reflected to suitable light detectors (not shown) for determination of the characteristics of each type of light.

Figure 5:
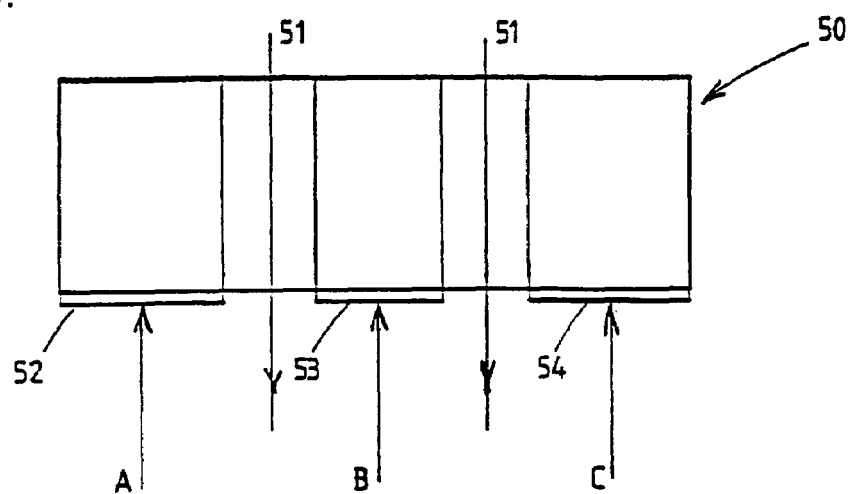
FIG. 5 is a cross-sectional view of a possible embodiment for a detector apparatus.

FIG. 5 illustrates a detector apparatus generally indicated by arrow 50 which may also be used to collect illumination from the paraboloid reflector shown in FIG. 2. In this embodiment the detector apparatus 50 may also provide for the transmission of light 51 from a light source (not shown) in a similar manner to the reflector apparatus described above in connection with FIGS. 3 and 4. The detector apparatus 50 may also have a number of light detectors 52, 53 and 54 spatially positioned so that they may receive the different types of light A, B and C incident on the reflector apparatus 50. Thus, the spatial orientation of the light detectors 52, 53 and 54 on the detector apparatus 50 allows for the discrimination between different types of light. On the other hand, where measurement of certain light is not desired, eg. light merely reflected from the light source, such light can be allowed to travel through the transmitting portion(s) 51 of the detector apparatus.

Figure 6:
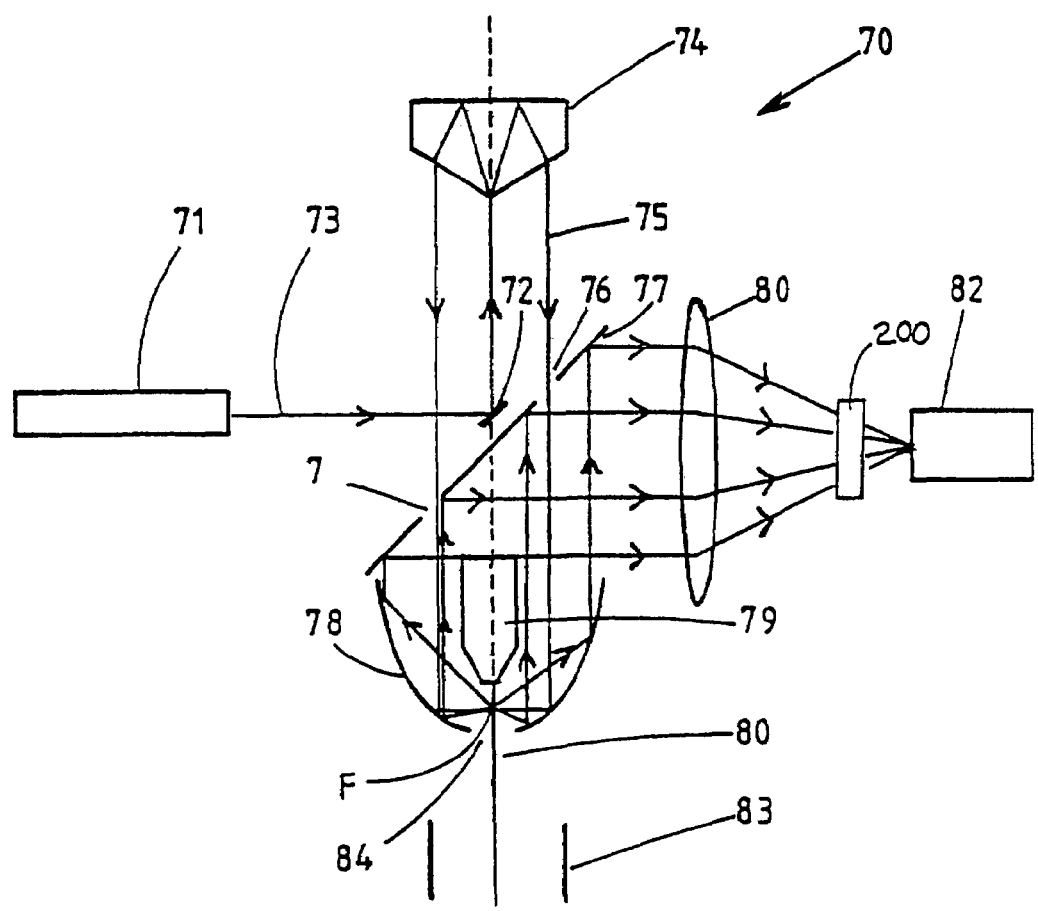
FIG. 6 is a cross-sectional view of one preferred embodiment of a flow cytometer in accordance with an aspect of the present invention.

FIG. 6 illustrates a first preferred embodiment of a flow cytometer generally indicated by arrow 70. The flow cytometer 70 includes the optical apparatus substantially as shown in FIG. 1. The optical apparatus includes an optical arrangement including a light source 71 and a mirror 72. The light source 71 produces collimated ultra-violet laser light 73 which is directed via mirror 72 to a prism 74 having a central axis. The prism 74 is configured to produce a cylinder of light 75 having a longitudinal axis coincident with the central axis of the prism. The prism may be the same as that indicated in FIG. 1(a) or (e) of the drawings. Alternatively, the prism may have a pyramidal face such as that shown in FIG. 1(d) to produce parallel beams of light evenly spaced from the central axis of the prism. The projected light 75 passes through an annular gap 76 in a second reflector 77 so as to be incident on the 45 degree point of a paraboloid reflector/collector 78. It will be seen in the following discussion that the reflector also services as a collector. For ease of reference the paraboloid reflector/collector 78 will be simply referred to as the paraboloid reflector 78. The paraboloid reflector 78 has an optical axis aligned with the central axis of the prism and a focus F lying on the optical axis.

Situated within the paraboloid reflector 78 is a nozzle assembly 79 which delivers a particle stream 80 e.g. sperm cells, which is substantially aligned with the optical axis of the paraboloid reflector and passes through an inspection zone located at the focus F. The nozzle assembly 79 delivers the sperm cells in a saline sheath solution and may utilize any of the known jet-in-air techniques to produce a laminar-flow particle stream with the sperm flowing single file through the inspection zone at F.

The paraboloid reflector 78 is designed with two criteria in mind. Firstly, the reflector should be able to withstand the corrosive environment introduced by the saline sheath environment. Secondly, the reflector should be designed to maximize reflectance of light of the UV frequency. Either of a rhodium reflective coating or an $AlSiO_2$ reflective coating on a nickel substrate were found to be effective.

The effect of the cylinder of light 75 being incident at the 45 degree point of the paraboloid mirror 78 is that it is reflected at 90 degrees so as to form a substantially coplanar disc of light which is convergent on the focal point F of the paraboloid reflector. Thus, this disc of light is able to interact with the particle stream 80 and illuminate the particles within the stream with substantially radially symmetric illumination.

If the particles have been stained with light-sensitive stain, the particles will fluoresce when illuminated. The use of stains is an accepted technique in sperm sexing since the number of molecules of stain bound will be equivalent to the number of molecules of DNA. This difference in uptake will yield a difference in the number of cells available for excitation and fluorescence. The difference in DNA content between X and Y sperm will yield a corresponding measurable difference in fluorescent light. Any of the known stains currently used for sperm sexing may be used. In particular, Hoechst 33342 which is of the bis-benzimidazole family shown below has been shown to provide the necessary X-Y differential resolution.

positioned before the photo-multiplier tube 82. Alternatively, the separation of frequencies may be achieved through the use of a dichroic mirror to reflect only those frequencies of interest. For example the dichroic mirror may be incorporated into the second reflector 77. However, if in certain applications it is desirable to measure scattered light, no filter is necessary.

It should be appreciated that instead of the single measurement detector 82 shown, an array of measurement detectors may be provided with an appropriate array of filters for measuring different forms of light. For example, the use of a second reflector in the form as that shown in FIG. 4 allows for the separation of light from different parts of the paraboloid reflector, it being possible to apply different filters to each of the separate light parts.

Light which has not interacted with the particles may be refracted by the medium which makes up the sample stream 80 and radiate as a disc in the opposite direction to the incoming light. As the particle stream will generally have a small diameter the resulting refraction of light by the medium will not be great. Thus, this light will substantially retrace the path of the illuminating cylinder of light and exit through the annular gap 76 in the second reflector 77. This creates a simple yet effective beam dump.

It should be appreciated that supporting structures of the components of the flow cytometer 70 including sample flow tubes for the nozzle assembly may obscure parts of the path for the cylinder of light 75. However, any resulting asymmetry in the disc of light is generally negligible and the cylinder of light is therefore still considered cylindrical. Optics might even be provided to refract an incident beam around obstructions.

The amount of light measured by the photo-multiplier tube is passed to a processor, e.g., a computer (not shown) to derive predetermined information such as an association between the amount of measured light and a property of the cell from each of at least some of the particles in the flow. This information is then correlated by a correlator, such as a computer, with the corresponding particle downstream of the inspection

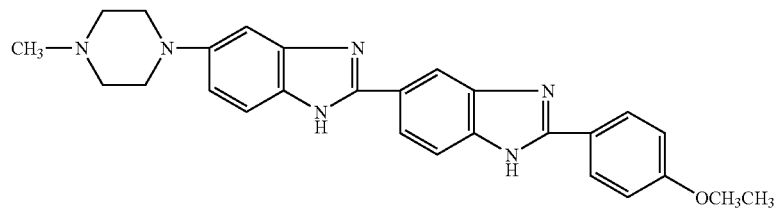

Thus, light which interacts with the particles will be scattered and/or fluoresced. This scattered and/or fluoresced light is then collected by the paraboloid reflector/collector 78 and reflected parallel to the optical axis of the paraboloid reflector 78. The second reflector 77 is positioned at a substantially 45 degree angle so as to reflect the scattered and/or fluoresced light towards a light detector in the form of a photomultiplier tube 82. The second reflector 77 as appropriate may comprise the forms illustrated in FIGS. 3-5.

For the specific application of the present invention in sexing sperm, the fluorescent light is of interest and the light merely scattered from the sperm in the sample stream may be of little or no interest. The fluorescent light will be of a different frequency and the separation of the two frequencies can be achieved through the use of a high pass filter 200 zone to enable sorting of the particle depending whether it meets certain selection criteria. For example, male and female sperm may be sorted by sex.

The flow sorting technique uses electrostatics to charge and deflect a cell containing droplet as it passes through an electric field. The droplet is created by a mechanical oscillation applied through a piezo-electric transducer thus perturbing the sample stream as it exits the nozzle 79. Each individual droplet can be charged depending on the characteristics of its contained particle just prior to break-off by application of a voltage to the carrier fluid. Depending on its charge, the droplet will be deflected from its normal gravitational trajectory by oppositely charged plates 83. To incorporate droplet sorting it may be necessary to provide a means by which to view the stream so as to count the number of droplet spacings between the inspection point (i.e. the focal point F) and the break-off point of the droplets. This can usually be achieved by inserting a small periscope through the aperture 84 in the base of the paraboloid reflector 78. Droplets which are not electrostatically deflected from the central path are collected directly below and flushed to waste.

Figure 7:
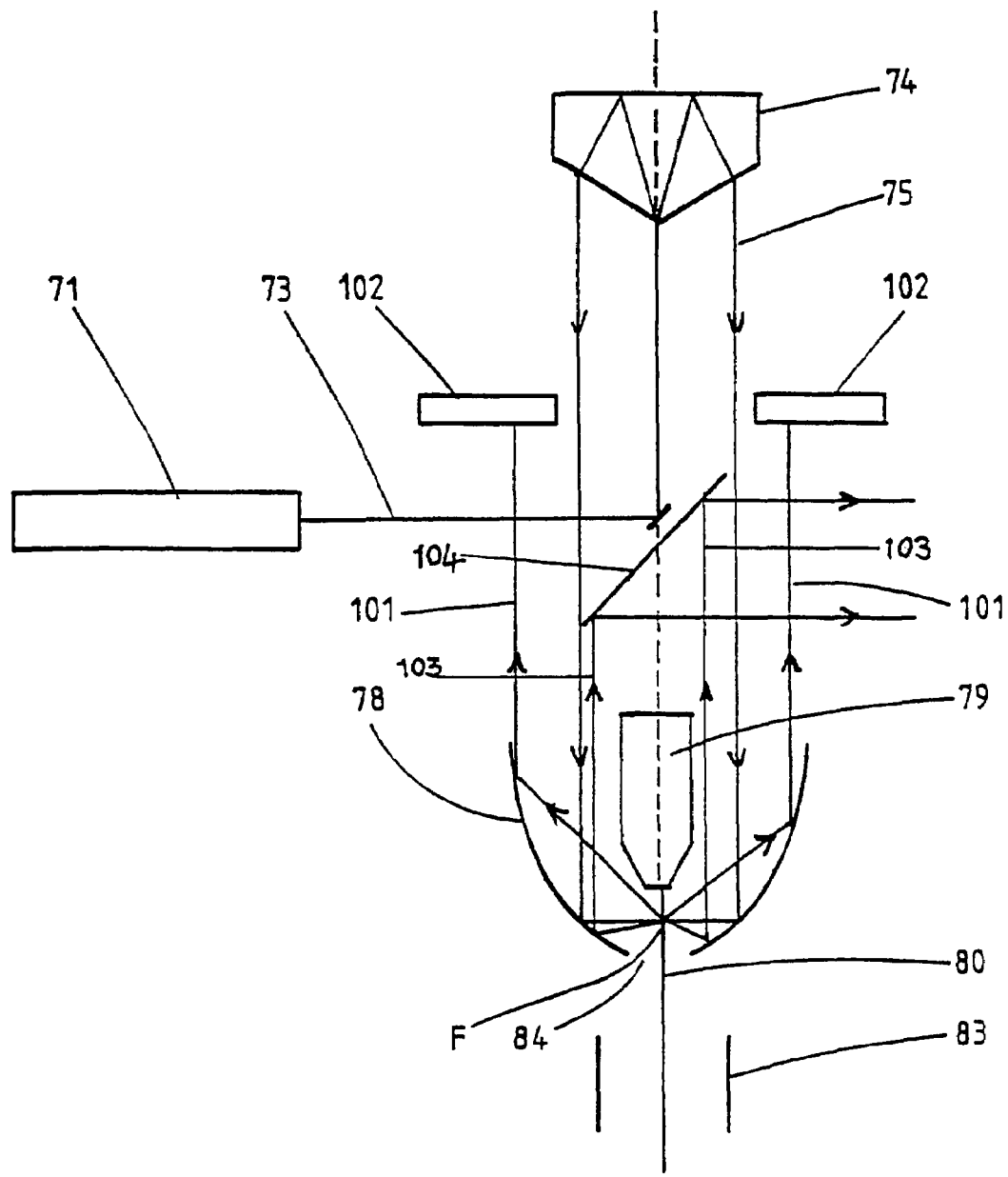
FIG. 7 is a cross-sectional view of a second embodiment of a flow cytometer in accordance with an aspect of the present invention.

In FIG. 7 there is provided an alternative flow cytometer generally indicated by arrow 100, this flow cytometer being substantially similar to the flow cytometer 70 shown in FIG. 6. Therefore, for ease of reference, similar numbering has been used to illustrate the components used in this embodiment.

The major difference with this embodiment shown in FIG. 7 is that only light 101 collected from the upper regions of the paraboloid reflector are received by the photomultipliers 102. Accordingly, the second reflector 77 need not be of the type discussed in the previous embodiment. Instead, only a continuous mirror confined within the cylindrical beam 75 need be used to reflect away the forward scattered an r fluoresced light 103.

On the otherhand, it should also be readily appreciated that where it is only desirable to consider forward scattered and/or fluoresced light, light measurement detectors may be suitable positioned so that they only receive this light.

During experimentation, it was found that an increase in sample to sheath differential pressure resulted in increased positional uncertainty of the particles through the focus, which results in a difference in illumination, and therefore fluorescence emission. There are a number of possible solutions which may be used either singly or in combination to broaden the focus around the sample stream.

The radial optics deliver a convergent disk of light at the excitation wavelength to the inspection point. Adjusting the vertical dimension of the radial focus is relatively simple if a concave or convex element is positioned in the laser beam in front of the axicon. However, broadening the focus laterally, while retaining sufficient light intensity at the focus for stain excitation and fluorescence, is not trivial.

To laterally broaden or defocus the radial focus requires that the illumination light cylinder be altered to cause divergence tangentially around its circular cross-section.

This would result in a lateral displacement of the incoming light disk thereby broadening the intensity distribution of the focal area. Some optical elements were proposed to perform this function. The first optical element would take the form of a radially etched diffraction grating. Such a component would successfully achieve the goal of lateral displacement with a minimal dispersive effect in the vertical profile of the focus. The second optical element is a light shaping diffuser element. Implementation of this element into the radial optics design would result in both vertical and lateral focus broadening. Other options include a diffractor or a cylindrical lens causing the beam to diffract sideways and broaden the focus.

Another approach is to use the focusing characteristics of the laser beam which is a Caussian beam where the depth of focus 1 is proportional to the focal length f and inversely proportional to the beam diameter D. The variable L is defined as the half-height width of the flex density profile as plotted along the optical axis. Thus, an increase in the focal length of the paraboloid reflector will cause an increase in d. Also, decreasing the diameter of the illuminating laser beam will bring about an increase in d.

In another embodiment of the invention, paraboloid and ellipsoidal configurations of reflectors can be used to provide illumination of an inspection zone of a linear flow of particles. One distinct advantage of this type of system is the ability to use a low cost arc lamp to replace the more expensive lasers commonly used in instruments of this type. Lasers are preferred in some devices because of the intensity of light that they can deliver. However, they have the disadvantage of only providing a specific wavelength of electromagnetic radiation. Arc lamps, however, are less expensive and can provide many different wavelengths of electromagnetic radiation in their emissions. Then, the proper wavelength can be selected by use of an inexpensive filter which filters out the undesired wavelengths of electromagnetic radiation.

Figure 8:
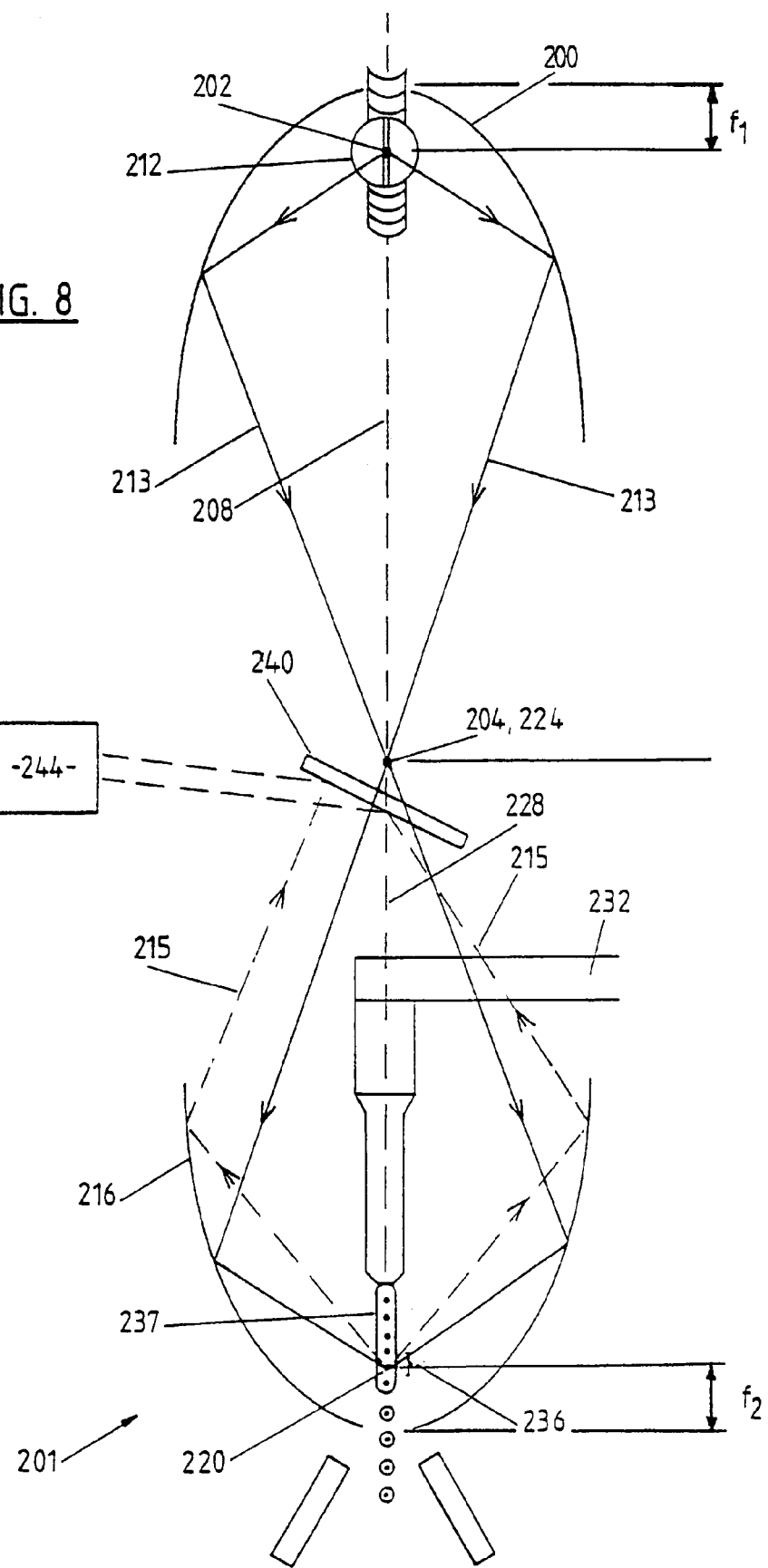
FIG. 8 is a cross-sectional view of a third embodiment of a flow cytometer in accordance with an aspect of the present invention.

Referring now to FIG. 8, an ellipsoidal embodiment of the invention can be seen.

FIG. 8 shows an analyzation instrument 20 1, such as a flow cytometer, in which a first reflector 200 having a partial ellipsoidal shape is disposed above a flow source which produces a flow 237 of particles to be analyzed. The reflector can be referred to as a partial ellipsoidal reflector as it is essentially a halved ellipsoid. Nevertheless, it is understood that given the contour of its surface it is recognized as ellipsoidal or similarly having a partial ellipsoidal shape. This first reflector 200 has both a near focal point 202 disposed near the top of the ellipsoid shown in FIG. 8 and a distant focal point 204 disposed below the partial ellipsoidal shape in FIG. 8. A central axis 208 of the partial ellipsoidal shape is defined by these two focal points.

A second reflector 216 can be disposed or oriented below the first reflector. Again, the second reflector can have a partial ellipsoidal shape. Furthermore, the partial ellipsoidal shape can have a near focal point 220 disposed near the bottom of FIG. 8 and a distant focal point 224 disposed overlapping or coincident with the distant focal point 204 of the first reflector. In addition, the partial ellipsoidal shape of the second reflector can have a central axis 228 defined by its near and distant focal points. Preferably, the central axis 208 of the first reflector is substantially aligned with the central axis 228 of the second reflector.

A source of electromagnetic radiation, such as an arc lamp 212 can be disposed at the near focal point of the first reflector 200. Due to the properties of an ellipsoid, electromagnetic radiation emitted by the source of electromagnetic radiation from the near focal point 202 and incident upon the first reflector 200 can be reflected back to the distant focal point of the first reflector. When the distant focal point 204 of the first reflector and the distant focal point 224 of the second reflector are coincident and the central axis 208 of the first reflector and the central axis 228 of the second reflector are collinear, this reflected light can continue on a path such that it is incident upon the second reflector 216. The second reflector 216 can then reflect the light which traveled through the distant focal point 224 of the second reflector to the near focal point 220 of the second reflector. In this fashion a real image of the source of electromagnetic radiation located at the near focal point 212 of the first reflector is created at the near focal point 220 of the second reflector 216. Therefore, a very intense light source can be concentrated on the inspection zone 236 of the linear flow of particles when the inspection zone is located at the near focal point 220 of the second reflector. Furthermore, this allows an arc lamp to be used—as a source with collimated beams, such as a laser, is unnecessary due to the ability of the reflectors to create a real image of the source of the electromagnetic radiation. Plus, a filter, such as a dichroic filter 240, can be used to filter out any wavelengths of undesired electromagnetic radiation.

When illuminated particles fluoresce, the fluorescence 215 can be reflected by the second reflector back towards a reflective surface, such as dichroic filter 240 which reflects the fluorescence to detector housing 244 to be detected. Because of the ellipsoidal geometry a converging set of beams is created—thus, there is no need for optics to focus the fluorescence on the detector. FIG. 8 also shows that a stream of cells can be deflected for sorting or analyzation purposes as they fall through an opening in the second reflector 216.

In FIG. 8, the first reflector and second reflector are shown having focal lengths of f1 and f2 respectively. When these focal lengths are equivalent and the distant focal points are coincident and the central axes are aligned as shown, the real image of the arc lamp will be the same size as the actual arc lamp. However, in some cases it is desirable to shrink the size of the real image of the arc source. This is the case when there is a possibility of two cells being very close to one another in the inspection zone of the stream. In such a case, it can be important to reduce a real image so that incident radiation is incident upon only the cell under analyzation and not a second cell nearby. This prevents fluorescence from a second cell which might give an incorrect analysis. There is more likelihood of cells being close by when the throughput of the analyzer is increased.

The arrangement of FIG. 8 could be used with only the bottom reflector and an alternative light source to illuminate the flow of particles. This might involve a laser directed at the flow of particles or off the reflective surface of the ellipsoidal reflector 216. This is a unique arrangement in flow cytometry, because the flow of particles is aligned coaxially with the central axis of the ellipsoidal reflector 216 to pass through the near focal point of the ellipsoidal reflector 216. After the flow of particles passes through the focal point at which the particles are irradiated with electromagnetic radiation for the purpose of analyzation, they can be sorted based upon their identifying characteristics. Electrostatic plates can be provided and disposed below the opening in the ellipsoidal reflective surface to deflect the particles as they pass close to or between the electrostatic plates. This embodiment is particularly unique in jet-in-air types of flow cytometers.

Figure 9:
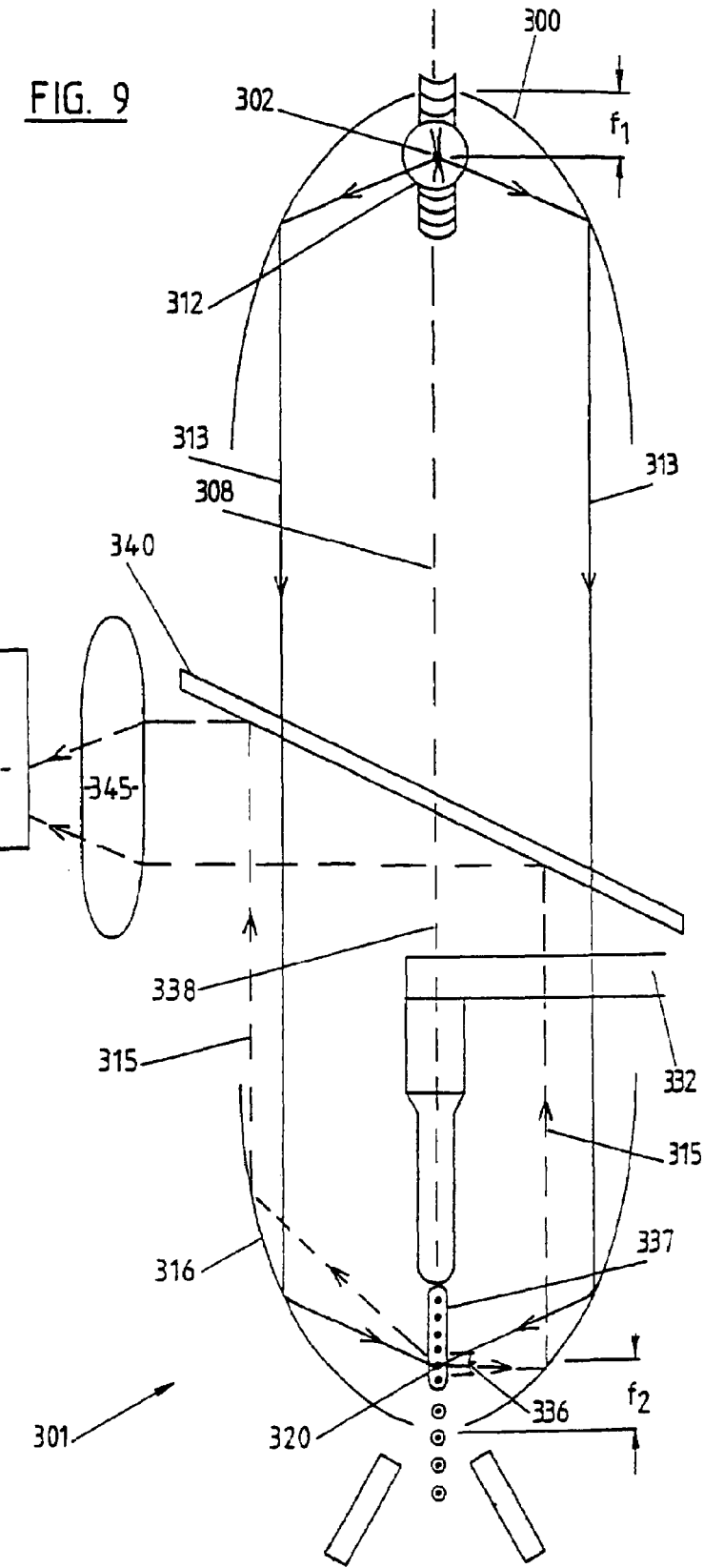
FIG. 9 is a cross-sectional view of a fourth embodiment of a flow cytometer in accordance with an aspect of the present invention.

In FIG. 9 a similar arrangement to that shown in FIG. 8 can be seen, the major difference being that paraboloid shapes are being used for the reflectors. A first reflector 200 having a partial paraboloid shape, a focal point (or focus) 302 is disposed to reflect electromagnetic radiation from a source of electromagnetic radiation, such as arc lamp 312. The source of electromagnetic radiation can be positioned at the focus of the paraboloid such that all emissions originating from the focus and incident on the partial paraboloid are reflected in collimated beams 313 toward a second reflector 316. The first reflector 300 and the second reflector 316 each have parabolic axes 308 and 338 respectively. These axes can be aligned such that a real image of the electromagnetic source appears at the focal point (or focus) 320 of the second reflector 316. A flow source 332 can provide a flow of particles 337 that flows through the focal point 320 of the second reflector 316. The portion of the flow of particles that flows through the focal point can be referred to as the inspection zone 336 upon which the electromagnetic radiation is focused so as to analyze a cell falling through the inspection zone.

When the incident electromagnetic radiation is incident upon a cell in the inspection zone, the stained cell can be caused to fluoresce. This fluorescence 315 can then be reflected by the second reflector 316 toward a reflector, such as dichroic mirror 340, which directs the fluorescence toward an optical apparatus 345 that focuses the fluorescence on a detector 344.

Once again, selection of equivalent focal lengths for the first reflector f1 and second reflector f2 will provide a real image of the arc lamp of the same size at the focal point of the second reflector. Similarly, choosing a focal length for the second reflector that is smaller than the focal length of the first reflector will result in a smaller image that will help prevent error when large throughput of cells is desired and consequently cells are close together at the inspection zone.

In FIGS. 8 and 9, one can see that plates can be provided to sort cells as they exit the ellipsoidal or paraboloid shapes.

Figure 10:
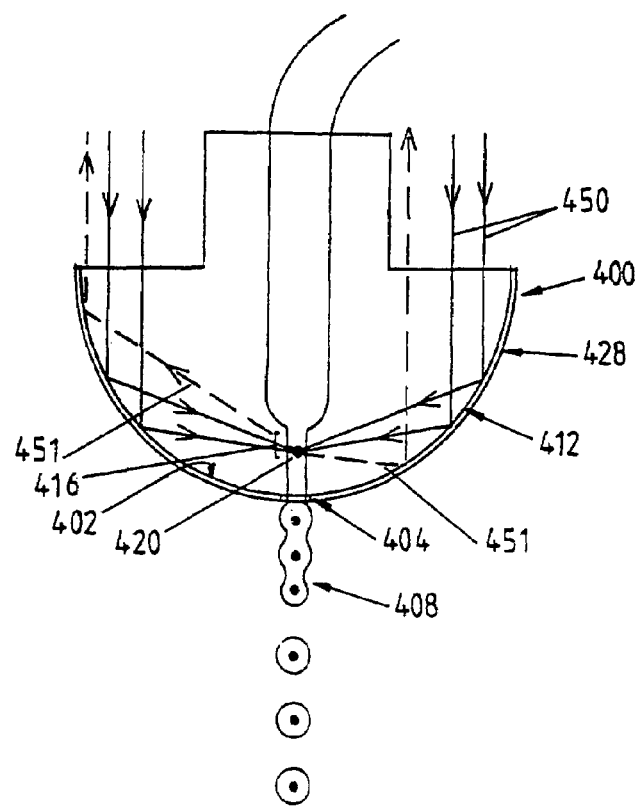
FIG. 10 is a cross-sectional view of a fifth embodiment of a flow cytometer in accordance with an aspect of the present invention.

In another embodiment of the invention, a nozzle 400 can be provided with a reflector coupled to the nozzle itself. In fact, the reflector can even be integral to the nozzle. This presents a significant advantage to the user of the analyzing apparatus as there is no need for alignment of the components since the coupling can accomplish that task. Referring to FIGS. 10, 11, 12 and 13 one can see how various embodiments of such a nozzle could be implemented. In FIG. 10, a paraboloid nozzle is shown. The nozzle can be manufactured of a material such as glass that permits the transmission of electromagnetic radiation, such as visible light. Incident beams of electromagnetic radiation from a source of electromagnetic radiation, such as a laser source 520 in FIG. 11 pass through the nozzle body and are incident on a reflector 402. The reflector 402 is coupled to the nozzle itself rather than existing separate from the nozzle. An opening 404 can be provided in the nozzle to allow a flow of particles 408 to flow through. The reflector 402 can be oriented to reflect the incident electromagnetic radiation at the flow of particles 408.

Two possible shapes which can be used for the reflective surface of the reflector are a paraboloid and an ellipsoid. In FIG. 10, a paraboloid reflective surface 412 is shown while in FIG. 11, an ellipsoidal reflective surface 512 is shown. As explained elsewhere, an inspection zone 416 can overlap a focal point(s) of the reflective surface, such as focal point 420 of the paraboloid of FIG. 10 to produce the desired reflection patterns.

Figure 11:
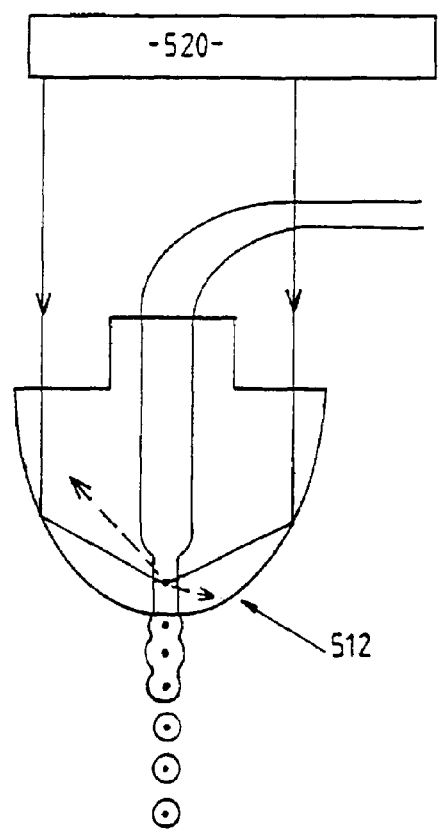
FIG. 11 is a cross-sectional view of a sixth embodiment of a flow cytometer in accordance with an aspect of the present invention.

The nozzle can be used with a source of electromagnetic radiation, such as a laser source 520 as shown in FIG. 11. However, it is also envisioned that an arc lamp or other source could be used as well. The source of electromagnetic radiation emits beams 450 which can be directed at the reflective surface. When the electromagnetic radiation is incident upon a cell under analysis, fluorescence is created as shown by beams 451.

Figure 12:
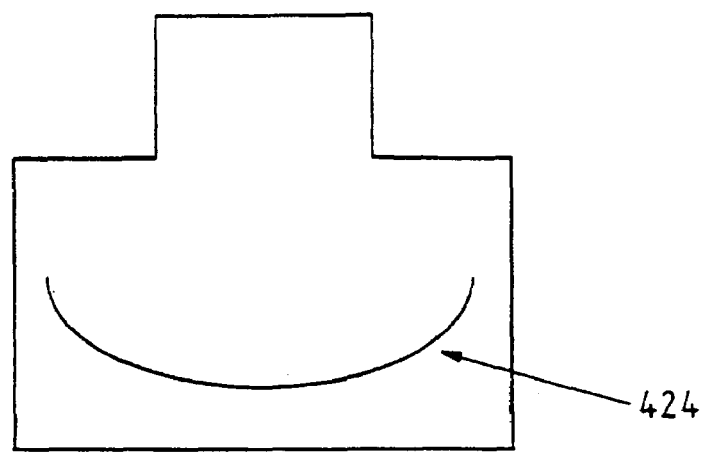
FIG. 12 is a cross-sectional view of a reflector incorporated into a flow nozzle design according to an aspect of the present invention.

To create the reflective surface, a variety of designs are possible. First, the nozzle body could be shaped in a paraboloid or ellipsoidal shape and then coated with a reflective material 428 applied to the nozzle surface. Additionally, a reflector, such as a metal reflector 424 could be inserted or embedded in the nozzle body as shown in FIG. 12. It might even be possible to rely on refractive properties which cause internal reflection or even total internal reflection.

Figure 13:
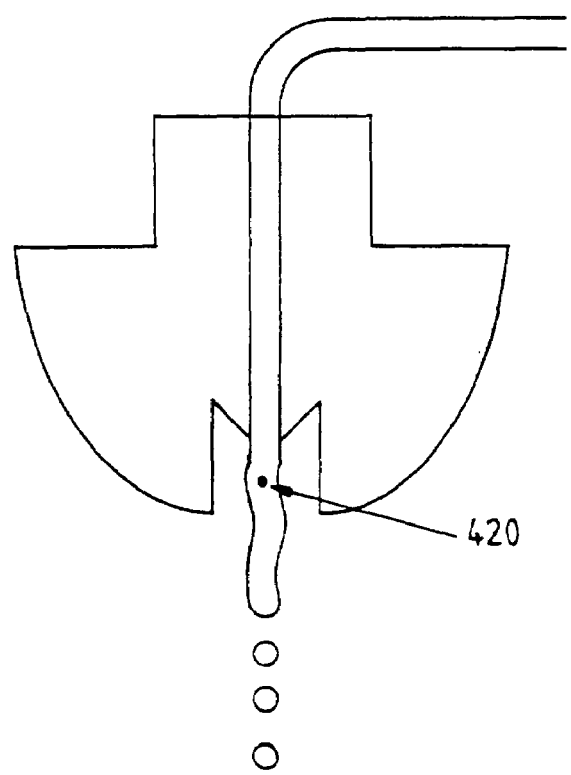
FIG. 13 is a cross-sectional view of a seventh embodiment of a flow cytometer in accordance with an aspect of the present invention.

In FIG. 13, an embodiment is shown in which the nozzle is shaped such that the focal point 420 of the reflective surface is external to the nozzle. External is intended to means outside of or away from the nozzle border, In such an embodiment, electromagnetic radiation could be directed at the focal point without needing to traverse through the nozzle body.

Figure 14:
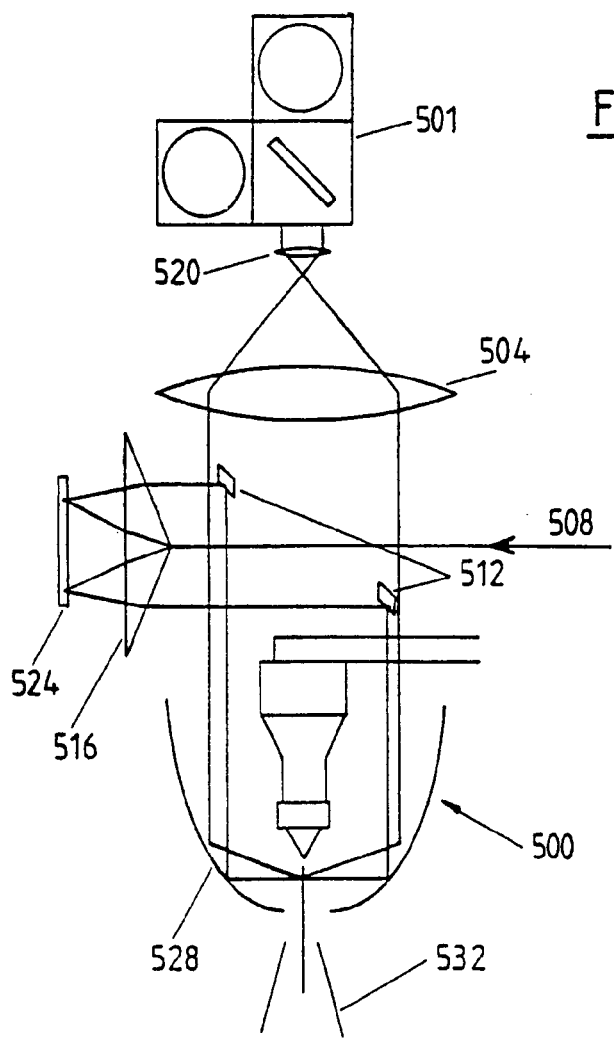
FIG. 14 is a cross-sectional view of an eighth embodiment of a flow cytometer in accordance with an aspect of the present invention.
Figure 15:
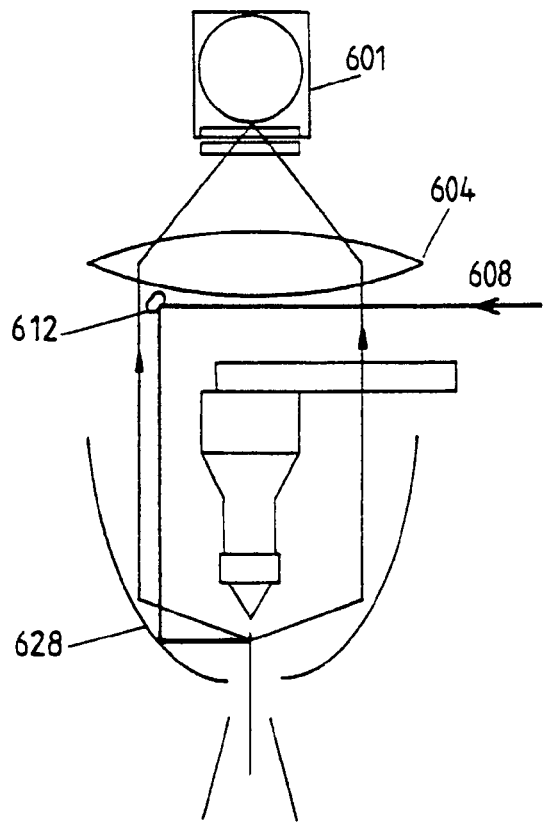
FIG. 15 is a cross-sectional view of a ninth embodiment of a flow cytometer in accordance with an aspect of the present invention.

Alternative embodiments of the invention can be seen in FIGS. 14 and 15. In FIG. 14, the radial optics configuration for a flow cytometer 500 can combine 360 degree radial illumination and radially symmetric collection of fluorescence from particles or cells as they pass through the inspection point. A glass cone 516 and a paraboloid reflector 528 can be used. The optical beam of a laser 508 can be steered onto the point of the glass cone. The beam can then be refracted into a divergent cone of light which is retro-reflected to produce a cylinder of laser light which encircles and is antiparallel to the input beam. This light cylinder can then be reflected by a 45 degree elliptical ring mirror 512 and aligned parallel to the optical axis of the paraboloid reflector 528. The angle of incidence of the cylindrical beam at the reflector is 45 degrees, causing the beam to form a coplanar convergent disk perpendicular to and focused on the sample stream.

Stained cells can be carried by the sample stream through the radial excitation focus and caused to fluoresce. Much of the fluorescence can be collected by the paraboloid reflector and projected out in a collimated beam onto an aspheric condensing lens 504. The lens can focus the fluorescent light to a spot which is imaged by a microscope objective 520 into a phomultiplier tube (PMT) 501 and filter housing. Optical alignment of specimens flowing through the focal region of the paraboloid reflector can be achieved by adjusting the flow cell position to maximize fluorescent signals from calibration microspheres. The paraboloid reflector can have a hole or opening in the base through which the sample stream can exit and where a jet observation camera and droplet sorting mechanism 532 can be situated.

In FIG. 15, a simplified version of the geometry of FIG. 14 is shown. The fluorescence collection elements can be retained to provide radially symmetric detection of cells as they pass through the inspection point of the flow cytometer. Excitation of cells can be performed by steering a laser beam 608 onto the paraboloid reflector 628 at an incidence angle that results in beam delivery from one direction similar to standard flow cytometer illumination. This can be accomplished by reflecting the beam off mirror 612. Detection of cells can be performed by a paraboloid reflector and aspheric lens combination. A single PMT, for example with a 40 OLP filter, can be positioned to collect all of the light focused by the aspheric lens. An additional neutral density filter (ND=1.3) can also be used to prevent saturation of the detector even at low PMT amplifier voltages.

The embodiment in FIG. 15 is particularly useful as it does not require as extensive an alignment of optics as is required in other embodiments. An ellipsoidal collector could also be used to deliver the laser light reflected from an adjusted mirror 612 and to reflect fluorescence to be collected at the PMT. The embodiments in FIG. 15 and are particularly advantageous because of the simplistic substantially coaxial alignment of the reflector with the detector.

It should be appreciated that the embodiments described in this description rely on physical arrangements that may not permit total or perfect collection, transmission, symmetry, reflection, alignment, etc. due to physical limitations of mirrors, optics and physical orientation of equipment. In view of these limits, such properties still may be considered at the very least as substantial.

The application also discloses the use of reflectors (20, 78, 216, 316, 400) having internal reflective surfaces shaped as three-dimensional figures of revolution, for example paraboloid or ellipsoid. The reflectors (20, 78, 216, 316) focus light incident onto the reflectors at one or more foci (F, 220, 320, 420). The reflectors may be used in combination with the optical apparatus including the prisms (1, 22, 24, 26, 28). The reflectors (20, 78, 216, 316) may be used in flow cytometers for focusing light at a sample stream (237, 337) passing through the focus (F, 220, 320, 420) of the reflector (20, 78, 216, 316). The collection of scattered and/or fluorescent light from an illuminated sample stream (237, 337) in a flow cytometer may be achieved with the use of a collector shaped as a figure of revolution e.g. paraboloid or ellipsoid.

Aspects of the present invention have been described by way of example only and it should be appreciated that modifications and additions may be made thereto without departing from the scope thereof.

As can be easily understood from the foregoing, the basic concepts of the present invention may be embodied in a variety of ways. It involves both optical techniques as well as devices to accomplish the appropriate optical technique. In this application, the optical techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in this or any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "reflector" should be understood to encompass disclosure of the act of "reflecting"—whether explicitly discussed or not—and, conversely, were there effectively disclosure of the act of "reflecting", such a disclosure should be understood to encompass disclosure of a "reflector" and even a "means for reflecting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the optical devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

In addition and as to computer aspects and each aspect amenable to programming or other electronic automation, the applicant(s) should be understood to have support to claim and make a statement of invention to at least: xvi) processes performed with the aid of or on a computer as described throughout the above discussion, xv) a programmable apparatus as described throughout the above discussion, xvi) a computer readable memory encoded with data to direct a computer comprising means or elements which function as described throughout the above discussion, xvii) a computer configured as herein disclosed and described, xviii) individual or combined subroutines and programs as herein disclosed and described, xix) the related methods disclosed and described, xx) similar, equivalent, and even implicit variations of each of these systems and methods, xxi) those alternative designs which accomplish each of the functions shown as are disclosed and described, xxii) those alternative designs and methods which accomplish each of the functions shown as are implicit to accomplish that which is disclosed and described, xxiii) each feature, component, and step shown as separate and independent inventions, and xxiv) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An optical apparatus comprising:
   a prism having a conical portion with an apex at a forward end of the prism and a central axis extending through the apex of the prism;

an optical arrangement including a source of electromagnetic radiation, the optical arrangement adapted to direct an incident beam of electromagnetic radiation onto the apex of the conical portion in a direction substantially aligned with the central axis of the conical portion; and
a reflective surface provided behind the apex of the prism;
such that the beam refracted by the prism will be reflected by the reflective surface back through the prism to project from the forward end of the prism as an annular beam of electromagnetic radiation.

2. An optical apparatus as described in claim 1 wherein the prism also includes a cylindrical base portion at a rear end thereof which has a cross-section corresponding to the base of the conical portion.

3. An optical apparatus comprising:
a prism having a pyramidal portion with an even number of inclined faces meeting at an apex at a forward end of the prism and a central axis extending through the apex; and
an optical arrangement including a source of electromagnetic radiation,
wherein the optical arrangement is adapted to direct an incident beam of electromagnetic radiation onto the apex of the pyramidal portion in a direction substantially aligned with the central axis of the pyramidal portion; and
a reflective surface provided behind the apex of the prism such that the beam refracted by the prism will be reflected by the reflective surface back through the prism to project from the forward end of the prism as a number of parallel beams.

4. An optical apparatus as described in claim 3 wherein the prism further includes a base portion at a rear end thereof which has a cross-section corresponding to the base of the pyramidal portion.

5. An optical apparatus as described in claim 1 or 3 wherein the reflective surface is provided at the rear end of the prism.

6. An optical apparatus as described in claim 2 or 4 wherein the reflective surface is provided at the rear end of the base portion.

7. An optical apparatus as described in claim 2 or 4 wherein the reflective surface is spaced from the base portion.

8. An optical apparatus as described in claim 7 wherein the spacing of the reflective surface from the base portion is adjustable.

9. An optical apparatus as described in claim 1 or 3 further comprising a paraboloid reflector having an internal paraboloidal shaped reflective surface, a focus and an optical axis, the reflector being oriented to receive on its reflective surface, the electromagnetic radiation projected from the forward end of the prism.

10. An optical apparatus as described in claim 9 further comprising a second reflector disposed between the prism and the paraboloid reflector, the second reflector having reflective portions to reflect the incident beam from the source onto the apex of the prism and one or more transmitting portions to transmit the beam(s) projected from the forward end of the prism.

11. An optical apparatus as described in claim 9 wherein the optical axis is substantially aligned with the central axis.

12. A flow cytometer that comprises the apparatus described in claim 9, wherein the flow cytometer further comprises a flow source to produce a flow of particles to be analyzed, the flow source being adapted to direct the flow of particles substantially through the focus or one of the foci of the internal paraboloidal shaped reflective surface.

13. A flow cytometer as described in claim 12 wherein the flow source is adapted to substantially align the flow with the optical axis of the internal paraboloidal shaped reflective surface.

14. A flow cytometer as described in claim 12 wherein an aperture is provided in the focusing reflector for passage of the flow beyond the paraboloid reflector.

15. A flow cytometer as described in claim 14 wherein the flow source includes a nozzle and wherein electrostatic droplet deflection sorting apparatus is provided below the aperture in the focusing reflector.

16. A flow cytometer as described in claim 12 wherein the source of electromagnetic radiation provides ultra violet light.

17. An optical apparatus comprising:
an optical configuration adapted to produce:
(a) an annular beam of electromagnetic radiation having a central beam; or
(b) plurality of beams of electromagnetic radiation having a central beams axis with which each of said plurality of beams is parallel, wherein each of said plurality of beams are evenly spaced from said central beams axis; and
a focusing reflector having an internal reflective surface having an optical axis and one or more foci, the reflector being oriented to substantially receive, onto its reflective surface, the annular beam or the plurality of beams of electromagnetic radiation.

18. An optical apparatus as described in claim 17 wherein the optical configuration is a reflective axicon.

19. An optical apparatus as described in claim 17 wherein the optical configuration is a waxicon.

20. An optical apparatus as described in claim 17 wherein the internal reflective surface is paraboloid in shape.

21. An optical apparatus as described in claim 17 wherein the optical axis of the internal reflective surface is substantially aligned with the central axis.

22. A flow cytometer that comprises the apparatus as described in claim 17, wherein the flow cytometer further comprises a flow source to produce a flow of particles to be analyzed, the flow source being adapted to direct the flow of particles substantially through the focus or one of the foci of the reflective surface.

23. A flow cytometer as described in claim 22 wherein the flow source is adapted to substantially align the flow with the optical axis of the internal reflective surface.

24. A flow cytometer as described in claim 22 wherein an aperture is provided in the focusing reflector for passage of the flow beyond the paraboloid reflector.

25. A flow cytometer as described in claim 24 wherein the flow source includes a nozzle and wherein electrostatic droplet deflection sorting apparatus is provided below the aperture in the focusing reflector.

26. A flow cytometer as described in claim 22 wherein the source of electromagnetic radiation provides ultra violet light.

27. An optical method comprising the steps of:
providing a prism having a conical portion with an apex at the forward end, a central axis extending through the apex and a reflective surface provided behind the apex of the prism; and
directing an incident beam of electromagnetic radiation onto the apex of the conical portion in a direction substantially aligned with the central axis of the conical portion to produce an annular beam of electromagnetic radiation projecting from the forward end of the prism.

28. An optical method comprising the steps of:
providing a prism having a pyramidal portion with an even number of inclined faces meeting at an apex at a forward end of the prism, a central axis extending through the apex and a reflective surface provided behind the apex of the prism; and
directing an incident beam of electromagnetic radiation onto the apex of the pyramidal portion in a direction substantially aligned with the central axis of the pyramidal portion to produce parallel beams of electromagnetic radiation projecting from the forward end of the prism.

29. An optical method as described in claim 27 or 28 further comprising the steps of:
orienting the paraboloid reflector such that it receives, onto its reflective surface, the one or more beams of electromagnetic radiation projected from the forward end of the prism; and
reflecting with a paraboloid reflector having an internal reflective surface of paraboloid shape, the reflective surface having an optical axis and a focus.

30. An method as described in claim 29 further comprising the step of:
substantially aligning the optical axis of the reflective surface with the central axis of the prism.

31. An method as described in claim 29 further comprising the step of directing a flow of particles to be analyzed through the focus of the paraboloid reflector.

32. An method as described in claim 31 further comprising:
substantially aligning the flow with the optical axis of the reflective surface.

33. An analyzation instrument comprising:
a flow source to produce a flow of particles to be analyzed, the flow source being adapted to direct the flow of particles through an inspection zone; and
an optical arrangement including a source of electromagnetic radiation, wherein the optical arrangement is adapted to converge the electromagnetic radiation as substantially coplanar, substantially radially symmetric electromagnetic radiation towards the inspection zone.

34. An analyzation instrument as described in claim 33 and further comprising a central axis along which the flow of particles is directed, wherein the optical arrangement is adapted to converge an annular disc of electromagnetic radiation symmetrically relative to the central axis.

35. A method of analyzing comprising the steps of:
providing a flow of particles to be analyzed;
directing the flow of particles to be analyzed through an inspection zone; and
converging electromagnetic radiation as substantially coplanar, substantially radially symmetric electromagnetic radiation towards the inspection zone.

36. A method as described in claim 35 and further comprising the step of converging an annular disc of electromagnetic radiation symmetrically relative to a central axis along which the flow of particles is directed.

* * * * *

UNITED STATES PATENT AND TRADEMARK OFFICE
CERTIFICATE OF CORRECTION

PATENT NO. : 7,586,604 B2  Page 1 of 1
APPLICATION NO. : 11/805572
DATED : September 8, 2009
INVENTOR(S) : Johnathan C. Sharpe et al.

It is certified that error appears in the above-identified patent and that said Letters Patent is hereby corrected as shown below:

On The Title Page,

Item (75) Inventor: "Jonathan C. Sharpe" should read --Johnathan C. Sharpe--

In the Specification,

Column 17, line 21, "On the otherhand, it should also be" should read --On the other hand, it should also be--

In the Claims,

Claim 30, column 27, line 22, "An method as described" should read --A method as described--

Claim 31, column 27, line 26, "An method as described" should read --A method as described--

Claim 32, column 28, line 1, "An method as described" should read --A method as described--

Signed and Sealed this
Twenty-third Day of December, 2014

Michelle K. Lee
*Deputy Director of the United States Patent and Trademark Office*